(12) United States Patent
Van Dun et al.

(10) Patent No.: US 7,645,835 B2
(45) Date of Patent: Jan. 12, 2010

(54) HIGH DENSITY ETHYLENE HOMOPOLYMERS AND BLEND COMPOSITIONS

(75) Inventors: Jozef J. Van Dun, Zandhoven (BE); Akira Miyamoto, Kurashiki (JP); Grant B. Jacobsen, Houston, TX (US); Fumio Matsushita, Kurashiki (JP); Patrick J. Schouterden, Wachtebeke (BE); Lee Spencer, Pearland, TX (US); Pak-Wing S. Chum, Lake Jackson, TX (US); Larry A. Meiske, Baton Rouge, LA (US); Peter L. Wauteraerts, Oostham (BE)

(73) Assignee: Dow Global Technologies, Inc., Midland, MI (US)

( * ) Notice: Subject to any disclaimer, the term of this patent is extended or adjusted under 35 U.S.C. 154(b) by 415 days.

(21) Appl. No.: 11/472,071

(22) Filed: Jun. 21, 2006

(65) Prior Publication Data

US 2006/0276593 A1 Dec. 7, 2006

Related U.S. Application Data

(60) Division of application No. 10/173,256, filed on Jun. 13, 2002, now Pat. No. 7,153,909, which is a division of application No. 08/857,817, filed on May 16, 1997, now abandoned, which is a continuation-in-part of application No. 08/555,436, filed on Nov. 9, 1995, now abandoned, which is a continuation-in-part of application No. 08/402,437, filed on Mar. 10, 1995, now abandoned, which is a continuation-in-part of application No. 08/340,989, filed on Nov. 17, 1994, now abandoned.

(51) Int. Cl.
*C08L 23/06* (2006.01)
*C08L 23/08* (2006.01)
*C08F 4/6592* (2006.01)

(52) U.S. Cl. ........................ 525/240; 525/53; 526/65; 526/124.3; 526/133; 526/134; 526/160; 526/161

(58) Field of Classification Search .................. 525/53, 525/240; 526/65, 124.3, 133, 134, 160, 161
See application file for complete search history.

(56) References Cited

U.S. PATENT DOCUMENTS

| | | | |
|---|---|---|---|
| 3,280,220 A | 10/1966 | Nelson | |
| 3,660,530 A | 5/1972 | Hoblit et al. | |
| 3,914,342 A | 10/1975 | Mitchell | |
| 4,230,831 A | 10/1980 | Sakurai et al. | |
| 4,314,912 A | 2/1982 | Lowery, Jr. et al. | |
| 4,426,316 A | 1/1984 | Gessell | |
| 4,438,238 A | 3/1984 | Fukushima et al. | |
| 4,526,943 A | 7/1985 | Fuentes, Jr. et al. | |
| 4,542,199 A | 9/1985 | Kaminsky et al. | |
| 4,544,647 A | 10/1985 | Fuentes, Jr. et al. | |
| 4,544,762 A | 10/1985 | Kaminsky et al. | |
| 4,547,475 A | 10/1985 | Glass et al. | |
| 4,547,551 A | 10/1985 | Bailey et al. | |
| 4,612,300 A | 9/1986 | Coleman, III | |
| 4,661,465 A | 4/1987 | Fuentes, Jr. et al. | |
| 4,783,512 A | 11/1988 | Gessell | |
| 4,798,081 A | 1/1989 | Hazlitt et al. | |
| 4,960,878 A | 10/1990 | Crapo et al. | |
| 5,008,204 A | 4/1991 | Stehling | |
| 5,015,749 A | 5/1991 | Schmidt et al. | |
| 5,041,583 A | 8/1991 | Sangokoya | |
| 5,041,584 A | 8/1991 | Crapo et al. | |
| 5,041,585 A | 8/1991 | Deavenport et al. | |
| 5,055,438 A | 10/1991 | Canich | |
| 5,057,475 A | 10/1991 | Canich et al. | |
| 5,064,802 A | 11/1991 | Stevens et al. | |
| 5,089,321 A | 2/1992 | Chum et al. | |
| 5,096,867 A | 3/1992 | Canich | |
| 5,132,380 A | 7/1992 | Stevens et al. | |
| 5,153,157 A | 10/1992 | Hlatkey et al. | |
| 5,189,106 A | 2/1993 | Morimoto et al. | |
| 5,240,894 A | 8/1993 | Burkhardt et al. | |

(Continued)

FOREIGN PATENT DOCUMENTS

| | | |
|---|---|---|
| DE | 3127133.2 | 1/1983 |
| EP | 277003 | 3/1988 |
| EP | 416815 | 3/1991 |
| EP | 468651 | 1/1992 |
| EP | 514828 | 11/1992 |

(Continued)

OTHER PUBLICATIONS

Zhou et al., *Polymer*, vol. 24, p. 2520, (1993).
Bohm et al., *Advanced Materials*, No. 3, p. 237, (1992).
X. Lu et al., *Polymer Testing II*, pp. 309-319. (1992).
Ramamurthy, *Journal of Rheology*, 30(2), pp. 337-357, (1986).
Shenoy, A.V., et al., *Rheological Acta*, pp. 22, 90, (1983).

(Continued)

*Primary Examiner*—Roberto Rábago

(57) ABSTRACT

Blend compositions containing a novel homopolymer, the use of which allows the incorporation of more comonomer in the additional components of the blend (for the same overall density) resulting in increased tie molecule formation and improvement in properties such as ESCR, toughness and impact strength are disclosed. The homopolymers are important for applications where a high density is needed to ensure certain mechanical properties like abrasion resistance, indentation resistance, pressure resistance, topload resistance, modulus of elasticity, or morphology (for the chlorination of PE to CPE) and additional advantages such as melt processability. The blend can be obtained by dry or melt mixing the already produced components, or through in-situ production by in parallel and/or in series arranged reactors. These resins can be used in applications such as films, blow molded, injection molded, and rotomolded articles, fibers, and cable and wire coatings and jacketings and, various forms of pipe.

11 Claims, No Drawings

U.S. PATENT DOCUMENTS

| | | | |
|---|---|---|---|
| 5,246,783 A | 9/1993 | Spenadel et al. | |
| 5,260,384 A | 11/1993 | Morimoto et al. | |
| 5,272,236 A | 12/1993 | Lai et al. | |
| 5,278,272 A | 1/1994 | Lai et al. | |
| 5,296,433 A | 3/1994 | Siedle et al. | |
| 5,322,728 A | 6/1994 | Davey et al. | |
| 5,350,723 A | 9/1994 | Neithamer et al. | |
| 5,374,696 A | 12/1994 | Rosen et al. | |
| 5,380,810 A | 1/1995 | Lai et al. | |
| 5,382,630 A | 1/1995 | Stehling et al. | |
| 5,382,631 A | 1/1995 | Stehling et al. | |
| 5,420,090 A | 5/1995 | Spencer et al. | |
| 5,446,001 A * | 8/1995 | Gurtzgen | 502/151 |
| 5,453,410 A | 9/1995 | Kolthammer et al. | |
| 5,470,993 A | 11/1995 | Devore et al. | |
| 5,486,632 A | 1/1996 | Devore et al. | |
| 5,942,586 A | 8/1999 | Herrmann et al. | |
| 6,114,477 A | 9/2000 | Merrill et al. | |
| 6,255,426 B1 | 7/2001 | Lue et al. | |

FOREIGN PATENT DOCUMENTS

| | | |
|---|---|---|
| EP | 520732 | 12/1992 |
| EP | 0 669 347 A1 | 8/1995 |
| EP | 776909 A1 | 6/1997 |
| EP | 783022 A1 | 7/1997 |
| WO | WO-90/03414 | 4/1990 |
| WO | WO-93/08221 | 4/1993 |
| WO | WO 93/21238 * | 10/1993 |
| WO | WO-94/07928 | 4/1994 |
| WO | WO-94/00500 | 6/1994 |
| WO | WO-94/25523 | 10/1994 |
| WO | WO-95/18160 | 6/1995 |
| WO | WO-96/16092 | 5/1996 |
| WO | WO-96/23005 | 8/1996 |
| WO | WO-96/28480 | 9/1996 |
| WO | WO-97/43323 | 11/1997 |

OTHER PUBLICATIONS

John Dealy, "Rheometers for Molten Plastics", pp. 97-99, (1982).
Wild et al., *Journal of Polymer Science, Poly. Phys. Ed.*, vol. 20, p. 441 (1982).
M.J. Cawood et al., *Polymer Testing 1*, pp. 3-7, (1980).
M. Shida, R.N. Shroff and L.V. Cancio, *Polymer Engineering Science*, vol. 17, No. 11, p. 770, (1977).
E. Plati et al., *Polymer Engineering and Science*, vol. 15, No. 6, pp. 470-477, Jun. 1975.
Williams et al., *Journal of Polymer Science, Polymer Letters*, vol. 6, p. 621, (1968).
Randall, *Review Macromol. Chem. Phys.*, C29 (2&3), pp. 285-297; 1989.
John Wiley and Sons, "Encyclopedia of Polymer Science and Engineering", vol. 6, pp. 472-477.
Research Disclosure No. 37644, 1995.

* cited by examiner

HIGH DENSITY ETHYLENE HOMOPOLYMERS AND BLEND COMPOSITIONS

CROSS REFERENCE TO RELATED APPLICATIONS

This application is a divisional of application Ser. No. 10/173,256, filed Jun. 13, 2002, now U.S. Pat. No. 7,153,909, which is a divisional of 08/857,817, filed May 16, 1997, now abandoned, which is a continuation-in-part of application Ser. No. 08/555,436, filed Nov. 9, 1995, now abandoned, which is a continuation-in-part of application Ser. No. 08/340,989, filed Nov. 17, 1994, now abandoned, and a continuation-in-part of application Ser. No. 08/610,647, filed Mar. 4, 1996, now U.S. Pat. No. 5,834,393, which is a continuation-in-part of application Ser. No. 08/402,437, filed Mar. 10, 1995, now abandoned.

STATEMENT REGARDING FEDERALLY SPONSORED RESEARCH OR DEVELOPMENT

Not Applicable

BACKGROUND OF THE INVENTION

The commercial polymerization of ethylene using coordination catalysts can be carried out in the high pressure, solution, slurry (suspension) or gas phase polymerization processes. The slurry and gas phase processes are examples of the so called particle form processes. In such systems, the catalyst for the polymerization is typically supported on an inert carrier. The polymerization is then carried out at temperatures below the melting point of the polymer, thereby precipitating the polymer onto the carrier. This results in the polymer powder particles growing while being suspended in either a diluent (slurry) or a fluidized polymer bed (gas-phase). The relatively low polymerization temperatures of these processes allows the manufacturer to produce polymers of very high molecular weight.

The most common ethylene polymerization catalysts are the chromium-based (so-called Phillips type) catalysts supported on silica(Cr—$SiO_2$), or the titanium based (so-called Ziegler type) catalysts supported on magnesium chloride ($MgCl_2$) and/or silica. However the relatively recent introduction of metallocene-based single site catalysts for ethylene/$\alpha$-olefin copolymerization has resulted in the production of new ethylene interpolymers (the term "interpolymer" is used herein to indicate a polymer wherein at least two different monomers are polymerized to make the interpolymer including copolymers, terpolymers, etc.). These single site catalysts include the bis(cyclopentadienyl)-catalyst systems as described by Hlatky et al in U.S. Pat. No. 5,153,157 and the constrained geometry catalysts. These catalysts and methods for their preparation are disclosed in U.S. application Ser. No. 545,403, filed Jul. 3, 1990 now abandoned (EP-A-416,815), European Patent Application EP-A-468,651; European Patent Application EP-A-514,828; U.S. application Ser. No. 876,268, filed May 1, 1992, now U.S. Pat. No. 5,721,185 (EP-A-520,732) as well as, U.S. Pat. No. 5,374,696, U.S. Pat. No. 5,470,993; U.S. Pat. No. 5,055,438, U.S. Pat. No. 5,057,475, U.S. Pat. No. 5,096,867, U.S. Pat. No. 5,064,802, and U.S. Pat. No. 5,132,380. In addition, certain cationic derivatives of the foregoing constrained geometry catalysts that are highly useful as olefin polymerization catalysts are disclosed and claimed in U.S. Pat. No. 5,132,380. In U.S. Pat. No. 5,453,410 combinations of cationic constrained geometry catalysts with an alumoxane were disclosed as suitable olefin polymerization catalysts. For the teachings contained therein, the afore-mentioned pending U.S. patent applications, issued United States Patents and published European Patent Applications are herein incorporated in their entirety by reference thereto.

In order for such catalysts to be used in the particle form processes, supported versions of constrained geometry catalysts have also been developed, such as those disclosed in WO 96/16092 and WO 96/28480 (the teachings contained therein, are herein incorporated in their entirety by reference). In these systems, the active form of the catalyst is strongly associated with the support and thus has no possibility of diffusing into the diluent during typical slurry process polymerization conditions.

A feature of these catalyst composition is the preparation of a solid component which can, as in WO 96/16092, comprise;

1) a silica support and an alumoxane in which the alumoxane is fixed to the support material by a heating and/or washing treatment, such that the alumoxane is substantially not extractable under severe conditions (toluene at 90° C.); and 2) a constrained geometry complex.

When the amount of extractable alumoxane is low, little can diffuse into the polymerization solvent or diluent if used, and thus little or no activation of the catalyst occurs in the diluent. Thus no appreciable amount of polymer will be formed in the diluent, as compared to polymer formed on the support material. If too much polymer is formed in the diluent the polymer bulk density will decrease below acceptable levels and reactor fouling problems may occur.

Alternatively, as in WO 96/28480, the solid (or supported) catalyst can be formed from;

1) a silica support material, which is treated with an organometallic metal alkyl compound (selected from Groups 2-13 of the Periodic Table of the Elements, germanium, tin, and lead); and 2) an activator compound which comprises a cation (which is capable of reacting with a transition metal compound to form a catalytically active transition metal complex) and a compatible anion having up to 100 nonhydrogen atoms and containing at least one substituent comprising an active hydrogen moiety; and 3) a constrained geometry complex.

The activator compound reacts with the metal alkyl compound through the active hydrogen-containing substituent. It is believed that the alkyl group of the metal alkyl compound combines with the active hydrogen moiety of the activator compound to release a neutral organic compound, for example an alkane, or hydrogen gas thereby chemically coupling the metal atom with the activator compound residue. Thus the activator is believed to become chemically attached to the support material. Upon addition of the constrained geometry complex, a supported catalyst is formed in which the active form of the catalyst is strongly associated with the support and remains there during the course of the polymerization conditions.

Additional advantages of polymers produced by single site catalysts as opposed to the more traditional Ziegler or Phillips (chromium on silica) catalysts relate to the nature of the catalyst residues remaining in the polymer after polymerization. Ziegler catalysts are typically prepared from chloride complexes of titanium such as $TiCl_4$ or $TiCl_3$ and are often supported on magnesium chloride ($MgCl_2$). Thus polymers produced by Ziegler catalysts often contain significant concentrations of magnesium chloride and other chloride containing catalyst residues in the polymer products. This can adversely effect the appearance of the film (due to "fish eye" formation) or cause corrosion problems with processing equipment. Similarly the products of the Phillips type (Cr on $SiO_2$) systems can contain chromium residues which if found at too high a level can limit the use of such resins for example in food contact applications Removal of such catalyst residues from the polymer can require the addition of expensive and time consuming post reactor polymer processing steps such as steam stripping or other methods of washing out the catalyst residues prior to polymer fabrication or sale.

The single site, and especially, the constrained geometry catalysts however are substantially chloride and chromium and free and, when supported, are usually supported on silica and not magnesium chloride and thus the resulting polymers have much lower (often zero) levels of chloride- and chromium-containing catalyst residues in their products, even in the absence of additional post reactor polymer washing steps Conventional supported Ziegler catalysts tend to produce polymers with relatively broad molecular weight distribution which varies with $M_w$. For instance Bailey et al. (U.S. Pat. No. 4,547,551, Phillips Petroleum) report that for a polymer with having an $M_n$ around 70000, produced by a magnesium chloride-supported Ziegler system with an organoaluminum cocatalyst, the $M_w/M_n$ is around 7.5. For ethylene homopolymers produced by Ziegler catalysts, the polymer density is also dependent upon molecular weight. The entropy that has to be overcome by crystallizing a longer homopolymer molecule is higher and more difficult to overcome than for a shorter homopolymer molecule. Consequently homopolymer density tends to decrease with increasing molecular weight. A typical Ziegler-Natta homopolymer having a melt index ($I_2$) of approximately 1 g/10 min will have a density higher than 0.960 g/cm$^3$.

The molecular weight distributions of homopolymers prepared using most supported or unsupported single site catalysts, which are not of the constrained geometry type, are smaller or equal to 3 over the complete molecular weight range. In addition, the density of such homopolymers is typically lower than the densities of the analogous homopolymers of the same molecular weight, prepared using Ziegler catalysts. This is exemplified by Stehling et al. (U.S. Pat. No. 5,382,631) which discloses, in sample designation '006 of Example 2, that a homopolymer, prepared under gas phase conditions using a supported single site catalyst, and having a melt index ($I_2$) of 5.0 g/10 min, has a density of only 0.9552 g/cm$^3$ and an $M_w/M_n$ of 2.80. Similarly Lux et al in Example 12 of WO 95/18160 using a supported single site catalyst disclose that a homopolymer, prepared under slurry process conditions, and having a melt index ($I_2$) of 0.2 g/10 min, has a density of only 0.9450 g/cm$^3$ and an $M_w/M_n$ of 2.77. This can be contrasted with the a typical Ziegler catalyst homopolymer product having an $I_2$, of 1.0 g/10 min, which will have a density greater than 0.9600 g/cm$^3$ and an $M_w/M_n$ much greater than about 3.

In many applications, it is highly desirable for a homopolymer to have a high density for improved toughness and stiffness. It is also highly desirable for such a high density homopolymer to have a relatively low $M_w/M_n$ (i.e. less than about 5) at low molecular weights (i.e. less than about 100,000). This minimizes the wax content of the polymer which otherwise can lead to die wax build up and smoke generation on extrusion and taste and odor problems in the resulting fabricated articles. It is also highly desirable for such a high density homopolymer to have a broader $M_w/M_n$ (i.e. greater than about 4) at higher molecular weights (i.e. greater than about 100,000) as an aid to processability of the polymer.

Thus homopolymers produced from Ziegler catalysts have the disadvantage of typically exhibiting a broad $M_w/M_n$ especially at low molecular weights.

Homopolymers derived from typical single site catalysts have the dual disadvantage of;

a) being unable to attain as high a density for a given molecular weight as comparable Ziegler products and;

b) exhibiting a narrow $M_w/M_n$ across the whole molecular weight range (which can limit processability especially at high polymer molecular weights).

Thus there remains a requirement for the production of ethylene homopolymers which, while having a high density, also have a narrow $M_w/M_n$ at low molecular weight and a broader $M_w/M_n$ at higher molecular weight.

Other uses of ethylene homopolymers involve their use as one of the components of blend compositions. It is known that improvement in impact and, environmental stress crack resistance (ESCR) of an ethylene copolymer, can be achieved by decreasing the comonomer content of the low molecular weight fraction of the ethylene copolymer to a level as low as possible while increasing the comonomer content of the high molecular weight fraction of the ethylene copolymer to a level as high as possible. It has also been demonstrated (as for example by Zhou et al, Polymer, Vol 24, p. 2520 (1993)), that large strain properties such as toughness tear, impact and ESCR can also be improved by the presence of "tie molecules" in the resin. High molecular weight molecules with the highest comonomer content (i.e. the highest degree of short chain branching) are responsible for the formation of most of the tie molecules upon crystallization.

Thus attempts to maximize properties such as toughness, modulus, impact strength and ESCR, without sacrificing processability, has resulted in the preparation and use of blend compositions made out of two or more polymer components of differing molecular structures. Blends containing solely Ziegler catalyst products are described in a number of patents.

For example, Nelson (U.S. Pat. No. 3,280,220, Phillips Petroleum) teaches that a blend of an ethylene homopolymer of low molecular weight (formed in the solution process) and an ethylene-butene-1 copolymer of high molecular weight (formed in a particle form process) provides higher ESCR advantageous for containers (bottles) and pipe than similar blends of copolymers.

Hoblitt et al. (U.S. Pat. No. 3,660,530, The Dow Chemical Company) teaches a method where part of the homopolymer produced after a first reaction step is subjected to 1-butene. The still active catalyst then produces a block copolymer of polyethylene and polymerized butene-1. Both components are then admixed. The resultant blend has improved ESCR properties.

Fukushima et al. (U.S. Pat. No. 4,438,238) disclose blends consisting of components with densities between 0.910 and 0.940 g/cm$^3$ and broad molecular weight and blend distributions substantially not having long chain branches have been found to have good processability similar to high pressure polyethylene Bailey et al. (U.S. Pat. No. 4,547,551) teach that ethylene polymer blends of a high molecular weight ethylene polymer, preferably an ethylene-mono-α-olefin copolymer, and a low molecular weight ethylene polymer, preferably an ethylene homopolymer, both preferentially with a narrow molecular weight distribution and low levels of long chain branching exhibit excellent film properties and a better balance of stiffness and impact and environmental stress cracking resistance (ESCR), superior to that expected for polyethylene of comparable density and flow.

Morimoto et al. (U.S. Pat. Nos. 5,189,106, and 5,260,384) disclose blends consisting of a high molecular weight copolymer in combination with a low molecular weight homopolymer have been found to possess good processability and excellent low temperature mechanical properties.

Boehm et al., (Advanced Materials 4 (1992) No 3, p 237), disclose the cascade polymerization process in which the comonomer is introduced in the high molecular weight fraction of the polymer resulting in a larger amount of comonomer being present at the same overall density. This in turn results in a polymer composition having improved rigidity-lifetime (failure time) compared to conventional unimodal copolymers. Several patents have also appeared teaching the process to produce such materials in a cascade process such as EP 0 022 376 (Morita et al).

Finally, Sakurai et al (U.S. Pat. No. 4,230,831) disclose that it is beneficial to mix low density polyethylene with various blend compositions to improve polymer die swell or melt tension.

Blend compositions of homogeneous interpolymers having narrow molecular weight distribution and narrow composition distributions are also known. Stehling et al. in U.S. Pat. Nos. 5,382,630 and 5,382,631 describe polymer compositions made by blending components which have $M_w/M_n$ of less than 3 and a Composition Distribution Breadth Index of $\geq 50\%$. The components are said to be produced by using metallocene catalyst systems known to provide narrow composition distributions and narrow molecular weight distributions.

Blend compositions containing both Ziegler and single site catalyst products have also been disclosed. Research Disclosure No. 310163 (Anonymous) teaches that blends of Ziegler Natta- and metallocene-catalyzed ethylene copolymers when fabricated into cast films have improved optical, toughness, heat sealability, film blocking and unwind noise properties when compared with metallocene-catalyzed polymer alone.

Research Disclosure No. 37644 (Anonymous) teaches that blends of traditionally (Ziegler-Natta) catalyzed resins and resins made by single site metallocene catalysts display superior transverse direction tear and machine direction ultimate tensile properties useful in cast film applications.

WO 94/25523 (Chum et al.) teaches that films having synergistically enhanced physical properties can be made, when the film is a blend of at least one homogeneously branched ethylene/α-olefin interpolymer and a heterogeneously branched ethylene/α-olefin interpolymer. Films made from such formulated compositions have surprisingly good impact and tensile properties, and an especially good combination of modulus and toughness.

However, blends derived totally from Ziegler catalyzed products still have the problem that the low molecular weight component will generate a high amount of extractables because of the broad MWD, and the high molecular weight component does not have the desirable comonomer distribution to generate a high tie molecule distribution, although the molecular weight distribution is broad. Blends derived from products prepared using conventional supported single site catalysts are limited in the overall density that they can achieve for a given total comonomer content at a final molecular weight, relative to blends containing Ziegler catalyzed materials, as the traditional single site catalysts are unable to generate as high a homopolymer density for a given molecular weight as the Ziegler catalyzed materials.

However, for blends containing both single site and Ziegler catalyst products, if the low molecular weight homopolymer blend component is produced using a Ziegler catalyst, the homopolymer density will be high but its molecular weight distribution ($M_w/M_n$) will be broad leading to a high amount of extractables. If a narrow molecular weight distribution ($M_w/M_n$) single site catalyst product is used as the high molecular weight component of the blend it will not be capable of generating the same amount of tie molecules, because of the lack of very high molecular weight molecules, also its comonomer distribution will not be optimal. Conversely, if the low molecular weight component is a homopolymer produced with single site catalyst, the homopolymer density cannot be increased as desired. Also, the comonomer distribution of the high molecular weight Ziegler Natta material is not optimal, although its molecular weight distribution is broad.

There also remains a requirement for blend compositions which have a low molecular weight homopolymer component having a high density and an $M_w/M_n$ which increases with molecular weight, and a higher molecular weight component having an overall high comonomer content and wherein the lower the molecular weight of a copolymer fraction in the molecular weight distribution of a said higher molecular weight component, the lower the comonomer content of the copolymer fraction; and, in the other aspect, the higher the molecular weight of a fraction of said higher molecular weight component, the higher the comonomer content of the copolymer fraction.

Finally there also remains a requirement for the production of ethylene homopolymers and blend compositions which exhibit excellent stiffness and toughness with good ESCR, impact and modulus and exhibiting excellent processability while minimizing wax buildup on the die, smoke generation on the extruder on processing, and low extractables in the resin to minimize its taste and odor

BRIEF SUMMARY OF THE INVENTION

In one embodiment, the present invention provides:

An ethylene homopolymer having an $M_w/M_n$ ratio greater than about 2.5, a melt index ($I_2$) of from about 0.0001 to about 1000 g/10 min., a density which satisfies the following inequality;

$$\text{density}(g/cm^3) > 0.9611 + 0.0058 \log(I_2) - 0.00128 \log^2(I_2);$$

and an $M_w/M_n$ ratio which satisfies the following inequality;

$$M_w/M_n \leq 11.67 \log M_w - 43.67.$$

The present invention also provides;

An ethylene homopolymer prepared by a process, which process comprises polymerizing ethylene under slurry process conditions with a catalyst comprising;

(I) a supported catalyst component resulting from admixing:
  (A) a support material;
  (B) an organometal compound which is a member of Groups 2-13 of the Periodic Table of the Elements, germanium, tin, or lead;
  (C) an activator compound containing a cation which is capable of reacting with a transition metal compound to form a catalytically active transition metal complex, and a compatible anion having up to 100 non-hydrogen atoms and containing at least one substituent comprising an active hydrogen moiety; and
  (D) a transition metal compound; or (II) a supported catalyst component resulting from admixing
(A) a support material and an alumoxane which component contains 15 to 40 weight percent of aluminum, based on the total weight of the support material and alumoxane, which is obtained by;
(a) heating said support material and alumoxane under an inert atmosphere for a period and at a temperature sufficient to fix alumoxane to the support material, to provide a supported catalyst component wherein not more than about 10 percent aluminum present in the supported catalyst component is extractable in a one-hour extraction with toluene at 90° C. using about 10 ml toluene per gram of supported catalyst component; and
(b) optionally, subjecting the product produced in step (a) to one or more wash steps to remove alumoxane not fixed to the support material; and
(B) a transition metal compound; or
(III) any combination of I and II.

The present invention also provides;
A polymer blend composition comprising;
(A) an ethylene homopolymer in an amount of from about 1 to about 99% by weight based on the combined weight of Components (A) and (B), having an $M_w/M_n$ ratio (as measured by GPC) greater than about 2.5, a density which satisfies the following inequality;

$$\text{density}(g/cm^3) > 0.9611 + 0.0058 \log(I_2) - 0.00128 \log^2(I_2);$$

and an $M_w/M_n$ which satisfies the following inequality;

$$M_w/M_n \leq 11.67 \log M_w - 43.67; \text{ and}$$

(B) an ethylene homopolymer other than one of Component A having the identical properties or an ethylene/α-olefin copolymer in an amount of from about 1 to about 99% by weight based on the combined weight of Components (A) and (B).

The present invention also provides;
A process for forming a polymer blend composition, which process comprises the steps of:
(1) preparing an ethylene homopolymer (A) having a density of from about 0.945 to about 0.980 g/cm³; a melt index ($I_2$) of from about 0.01 to about 3000 g/10 min; an $I_{10}/I_2$ ratio of from about 5.5 to about 25 or an $I_{21}/I_2$ ratio of from about 20 to about 50; an $M_w/M_n$ ratio is from about 3 to about 6; wherein said homopolymer contains less than about 1 ppm catalyst chloride residues and less than about 1 ppm catalyst chromium residues;
(II) contacting under polymerization conditions a feedstream comprising ethylene, optionally at least one α-olefin comonomer, and an ethylene polymerization catalyst, to form (B) an ethylene homopolymer or ethylene/α-olefin interpolymer; and
(III) combining the ethylene homopolymer (A) with the ethylene homopolymer or ethylene/α-olefin interpolymer (B) to form (C) the polymer blend composition The properties of the homopolymers of the present invention are important for applications where a high density is needed to ensure certain mechanical properties like abrasion resistance, indentation resistance, pressure resistance, top-load resistance, modulus of elasticity, or morphology (for the chlorination of PE to CPE) and additional advantages such as melt processability.

Advantages of using the homopolymer in blend compositions is that, for a given molecular weight, its increased density over prior art ethylene homopolymers allows the incorporation of more comonomer in the second component of the blend. This, in turn, results in increased tie molecule formation and improvement in properties such as ESCR, toughness and impact strength. The blend can be obtained by dry or melt mixing the already produced components, or through in-reactor production using multiple reactors which can be autoclave or loop reactors in either parallel and/or series configurations.

These resins can be used in applications improved impact resistance, improved modulus of elasticity, high slow and rapid crack propagation resistance, improved ball indentation hardness and improved notched impact strength are desired. Such applications include, but are not limited to, sintering powders (where ultra high molecular weight polyethylene powder is incorporated as a fused component of surfaces which are required to have high abrasion resistance including gear wheels of machinery, and the lower surfaces of ski's). CPE feedstock resins, films, blow molded, injection molded, and rotomolded articles, fibres, and cable and wire coatings and jacketings and, various pipe applications.

These and other features of the present invention will become better understood with reference to the following descriptions and appended claims.

DETAILED DESCRIPTION OF THE INVENTION

Definitions.
All references herein to elements or metals belonging to a certain Group refer to the Periodic Table of the Elements published and copyrighted by CRC Press, Inc., 1989. Also any reference to the Group or Groups shall be to the Group or Groups as reflected in this Periodic Table of the Elements using the IUPAC system for numbering groups.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The term "hydrocarbyl" as employed herein means any aliphatic, cycloaliphatic, aromatic, aryl substituted aliphatic, aryl substituted cycloaliphatic, aliphatic substituted aromatic, or aliphatic substituted cycloaliphatic groups.

The term "hydrocarbyloxy" means a hydrocarbyl group having an oxygen linkage between it and the carbon atom to which it is attached.

The term "silyl" means a group having a silicon linkage between it and the carbon atom to which it is attached.

The term "germyl" means a group having a germanium linkage between it and the carbon atom to which it is attached.

The term "Bronsted Acid cation" means a cation which acts as a proton donor.

The term "interpolymer" is used herein to indicate a polymer wherein at least two different monomers are polymerized to make the interpolymer. This includes copolymers, terpolymers, etc.

Test Methods.

a) Density and Melt Flow Measurements.

The density of the polymer compositions for use in the present invention was measured in accordance with ASTM D-792. The molecular weight of the polymer compositions for use in the present invention is conveniently indicated using a melt index measurement according to ASTM D-1238, Condition 190° C./2.16 kg (formally known as "Condition (E)" and also known as $I_2$) was determined, as were conditions 190° C./5 kg, 10 kg and 21.6 kg known as $I_5$, $I_{10}$, and $I_{21}$ respectively. Melt index is inversely proportional to the molecular weight of the polymer. Thus, the higher the molecular weight, the lower the melt index, although the relationship is not linear. Other useful physical property determinations made on the novel polymer compositions described herein include the melt flow ratio (MFR): measured by determining "$I_{10}$" (according to ASTM D-1238, Condition 190° C./10 kg (formerly known as "Condition (N)") and dividing the obtained $I_{10}$ by the $I_2$. The ratio of these two melt index terms is the melt flow ratio and is designated as $I_{10}/I_2$. Other melt flow ratios measured include $I_{21.6}/I_5$, and $I_{21.6}/I_2$.

b) Gel Permeation Chromatograhy.

The molecular weight ($M_w$) and distributions ($M_w/M_n$) of the homopolymer and the various blends of the present invention were determined by gel permeation chromatography (GPC) on a Waters 150 C high temperature chromatographic unit equipped with mixed porosity columns, operating at a system temperature of 140° C. The solvent was 1,2,4-trichlorobenzene, from which 0.3 percent by weight solutions of the samples were prepared for injection. The flow rate was 1.0 milliliters/minute and the injection size was 100 microliters.

The molecular weight determination was deduced by using narrow molecular weight distribution polystyrene standards (from Polymer Laboratories) in conjunction with their elution volumes. The equivalent polyethylene molecular weights were determined by using appropriate Mark-Houwink coefficients for polyethylene and polystyrene (as described by Williams and Ward in *Journal of Polymer Science, Polymer Letters*, Vol. 6, (621) 1968) to derive the following equation:

$$M_{polyethylene}=a*(M_{polystyrene})^b.$$

In this equation, a=0.4316 and b=1.0. Weight average molecular weight, $M_w$, and number average molecular weight, $M_n$, was calculated in the usual manner according to the following formula:

$M_j=(\Sigma w_i(M_i)^j)$; where $w_i$ is the weight fraction of the molecules with molecular weight $M_i$ eluting from the GPC column in fraction i and j=1 when calculating $M_w$ and j=−1 when calculating $M_n$.

c) Cross Fractionation Chromatography (CFC)

The cross fraction chromatography (CFC) of the ethylene interpolymer components of the blend compositions of the present invention was conducted using a CFC T-150A (manufactured and sold by Mitsubishi Kagaku Corp., Japan). The measurement by CFC was conducted as follows. 20 mg of a sample was dissolved in 20 ml of dichlorobenzene having a temperature of 140° C., to thereby obtain a solution of the sample. Then, 5 ml of the obtained solution was added to a TREF (temperature rising elution fractionation) column filled with glass beads, and the solution allowed to cool to 0° C. at a rate of 1° C./min. Subsequently, the solution was heated, so as to elevate the temperature of the solution at a rate of 1° C./min, thereby extracting copolymer fractions. Then, the extracted copolymer fractions were subjected to gel permeation chromatography (GPC) using a GPC column Shodex AD806MS (manufactured and sold by Showa Denko K.K., Japan), followed by Fourier Transform Infrared Spectroscopy (FT-IR) using Nicolet Manga—IR Spectrometer 550 (manufactured and sold by Nicolet Co., Ltd., U.S.A.).

For the cross fractionation chromatography (CFC) of the ethylene interpolymer components of the blend compositions of the present invention, with respect to extraction at an arbitrary temperature T(° C.) falling within the range of between a first temperature at which a maximum amount of extraction is exhibited and a second temperature which is 10° C. higher than the first temperature, the relationship between the arbitrary temperature T(° C.) and a point in molecular weight on a molecular weight distribution profile of a copolymer fraction extracted at the arbitrary temperature T(° C.) at which point in molecular weight the molecular weight distribution profile of the copolymer fraction shows a peak having a maximum intensity is treated by the least squares method to obtain an approximate straight line, the approximate straight line has a gradient within the range defined by the formula:

$$\{\log Mp(T^1)-\log Mp(T^2)\}/(T^1-T^2)$$

wherein $T^1$ and $T^2$ are two different arbitrary extraction temperatures T(° C.) within the range of between the first temperature and the second temperature, and $Mp(T^1)$ and $Mp(T^2)$ are, respectively, molecular weights corresponding to $T^1$ and $T^2$ on the approximate straight line.

d) Molecular Weight Distribution Profile and the Comonomer Content Distribution.

The comonomer content distribution profile was obtained by subjecting the ethylene interpolymers to gel permeation chromatography/Fourier transformation infrared spectroscopy (GPC/FT-IR). In the present invention, the measurement by GPC was conducted using 150 C ALC/GPC (manufactured and sold by Waters Assoc. Co. U.S.A.), in which three columns [one Shodex AT-807s (manufactured and sold by Showa Denko K.K., Japan) and two TSK-Gel GMH-H6 (manufactured and sold by Tosoh Corp., Japan)], connected in series, were used, and the measurement by FT-IR was conducted by dissolving 20 to 30 mg of a sample in 15 ml of trichlorobenzene having a temperature of 140° C., and applying 500 to 1,000 μl of the resultant solution to an FT-IR apparatus (Perkin-Elmer 1760X, manufactured and sold by Perkin Elmer Cetus, Co., Ltd., U.S.A.).

The comonomer content is defined as a value obtained by dividing the number of comonomer units relative to 1,000 methylene units contained in the copolymer, by 1,000. For example, when 5 comonomer units are contained relative to 1,000 methylene units, the comonomer content is 0.005. The value of the comonomer content can be obtained from the ratio of the intensity of an absorbance attributed to the comonomer units to the intensity of an absorbance attributed to the methylene units, which ratio can be obtained by FT-IR. For example, when a linear α-olefin is used as a comonomer, the ratio of the intensity of absorbance at 2,960 $cm^{-1}$, which is attributed to the methyl groups, to the intensity of absorbance at 2,925 $cm^{-1}$, which is attributed to the methylene groups, is obtained by FT-IR. From the obtained ratio, the comonomer content can be obtained.

Generally, the above-mentioned comonomer content distribution profile is shown as a line containing points indicating comonomer contents. For improving the accuracy of the profile, it is desirable to obtain a large number of points indicating the comonomer contents by repeatedly conducting the comonomer content measurement using the same sample under the same conditions. In the present invention, within the above-defined range in molecular weight of the ethylene copolymer, an approximate straight line is obtained from the obtained points of comonomer content distribution profile by the least squares method.

In the present invention, the gradient of the approximate straight line obtained from the comonomer content distribution profile was defined by the following formula:

$$\{C(Mc^1)-C(Mc^2)\}/(Log\ Mc^1-Log\ Mc^2)$$

wherein:

$Mc^1$ and $Mc^2$ are two different arbitrary points (Mc) in molecular weight which satisfy the formula (I), and $C(Mc^1)$ and $C(Mc^2)$ are, respectively, comonomer contents corresponding to $Mc^1$ and $Mc^2$ on the approximate straight line.

The Ethylene Homopolymers.

The ethylene homopolymers of the present invention can be produced under slurry process conditions with the supported constrained geometry catalysts as described hereinafter.

The Supported Constrained Geometry Catalysts.

The preferred catalyst systems to be used in the present invention comprise a constrained geometry catalyst (a) and a solid component (b).

(a) The Constrained Geometry Catalysts.

Exemplary single site catalysts comprise a transition metal complex corresponding to the formula:

$$L_lMX_pX'_q$$

that has been or subsequently is rendered catalytically active by combination with an activating cocatalyst or by use of an activating technique, wherein;

M is a metal of Group 4 of the Periodic Table of the Elements having an oxidation state of +2, +3 or +4, bound in an $\eta^5$ bonding mode to one or more L groups;

L independently each occurrence is a cyclopentadienyl-, indenyl-, tetrahydroindenyl-, fluorenyl-, tetrahydrofluorenyl-, or octahydrofluorenyl-group optionally substituted with from 1 to 8 substituents independently selected from the group consisting of hydrocarbyl, halo, halohydrocarbyl, aminohydrocarbyl, hydrocarbyloxy, dihydrocarbylamino, dihydrocarbylphosphino, silyl, aminosilyl, hydrocarbyloxysilyl, and halosilyl groups containing up to 20 non-hydrogen atoms, or further optionally two such L groups may be joined together by a divalent substituent selected from hydrocarbadiyl, halohydrocarbadiyl, hydrocarbyleneoxy, hydrocarbyleneamino, siladiyl, halosiladiyl, and divalent aminosilane, groups containing up to 20 non-hydrogen atoms;

X independently each occurrence is a monovalent anionic σ-bonded ligand group, a divalent anionic σ-bonded ligand group having both valences bonded to M, or a divalent anionic σ-bonded ligand group having one valency bonded to M and one valency bonded to an L group, said X containing up to 60 nonhydrogen atoms;

X' independently each occurrence is a neutral Lewis base ligating compound, having up to 20 atoms;

l is one or two;

p is 0, 1 or 2, and is 1 less than the formal oxidation state of M when X is an monovalent anionic σ-bonded ligand group or a divalent anionic σ-bonded ligand group having one valency bonded to M and one valency bonded to an L group, or p is 1+1 less than the formal oxidation state of M when X is a divalent anionic σ-bonded ligand group having both valencies bonded to M; and q is 0, 1 or 2.

Single site catalysts including the constrained geometry catalysts are believed to exist in the form of a mixture of one or more cationic or zwitterionic species derived from the metallocene-based transition metal coordination complexes in combination with an activating compound. Fully cationic or partially charge separated metal complexes, that is, zwitterionic metal complexes, have been previously disclosed in U.S. Pat. Nos. 5,470,993 and 5,486,632, the teachings of which are herein incorporated in their entirety by reference thereto.

The cationic complexes of single site catalysts are believed to correspond to the formula:

$$L_lM^+X_{p-1}A^-$$

wherein:

M is a Group 4 metal in the +4 or +3 formal oxidation state;

L, X, l and p are as previously defined; and $A^-$ is a noncoordinating, compatible anion derived from the activating cocatalyst.

The zwitterionic complexes in particular result from activation of a Group 4 metal diene complex that is in the form of a metallocyclopentene, wherein the metal is in the +4 formal oxidation state, (that is X is 2-butene-1,4-diyl, or a hydrocarbyl substituted derivative thereof, having both valencies bonded to M) by the use of a Lewis acid activating cocatalyst, especially tris(perfluoro-aryl)boranes. These zwitterionic complexes are believed to correspond to the formula:

$$L_lM^+X_{p-l}X^{**}-A^-$$

wherein:

M is a Group 4 metal in the +4 formal oxidation state;

L, X, l and p are as previously defined;

$X^{**}$ is the divalent remnant of the conjugated diene, X', formed by ring opening at one of the carbon to metal bonds of a metallocyclopentene; and $A^-$ is a noncoordinating, compatible anion derived from the activating cocatalyst.

As used herein, the recitation "noncoordinating" means an anion which either does not coordinate to the transition metal component or which is only weakly coordinated therewith remaining sufficiently labile to be displaced by a neutral Lewis base, including an α-olefin. A non-coordinating anion specifically refers to an anion which when functioning as a charge balancing anion in the catalyst system of this invention, does not transfer a fragment thereof to said cation thereby forming a neutral four coordinate metal complex and a neutral byproduct. "Compatible anions" are anions which are not degraded to neutrality when the initially formed complex decomposes and are noninterfering with desired subsequent polymerizations.

Preferred X' groups are phosphines, especially trimethylphosphine, triethylphosphine, triphenylphosphine and bis (1,2-dimethylphosphino)ethane; $P(OR)_3$, wherein R is as previously defined; ethers, especially tetrahydrofuran; amines, especially pyridine, bipyridine, tetramethyl-ethylenediamine (TMEDA), and triethylamine; olefins; and conjugated dienes having from 4 to 40 carbon atoms. Complexes including conjugated diene X' groups include those wherein the metal is in the +2 formal oxidation state.

Examples of coordination complexes used for single site catalyst preparation include the foregoing species:

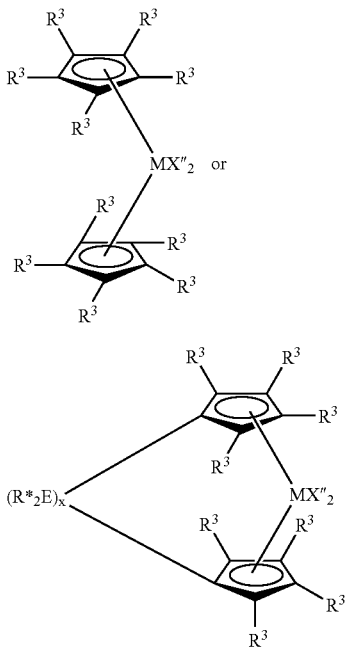

(I)

(II)

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (i.e., a hydrocarbadiyl, siladiyl or germadiyl group) thereby forming a fused ring system, X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, R* independently each occurrence is $C_{1-4}$ alkyl or phenyl, E independently each occurrence is carbon or silicon, and x is an integer from 1 to 8.

Additional examples of metal coordination complexes including the constrained geometry catalysts include those corresponding to the formula:

$$LMX_pX'_q \quad (III)$$

wherein L, M, X, X', p and q are as previously defined. A preferred metal complex belongs to the foregoing class (III) and corresponds to the formula:

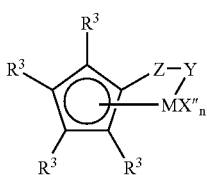

wherein:

M is titanium, zirconium or hafnium in the +2, +3 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (i.e., a hydrocarbadiyl, siladiyl or germadiyl group) thereby forming a fused ring system, each X" is a halo, hydrocarbyl, hydrocarbyloxy, hydrocarbylamino, or silyl group, said group having up to 20 non-hydrogen atoms, or two X" groups together form a neutral $C_{5-30}$ conjugated diene or a divalent derivative thereof;

Y is —O—, —S—, —NR*—, —PR*—;

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein R* is as previously defined, and n is an integer from 1 to 3.

Most preferred coordination complexes used according to the present invention are complexes corresponding to the formula:

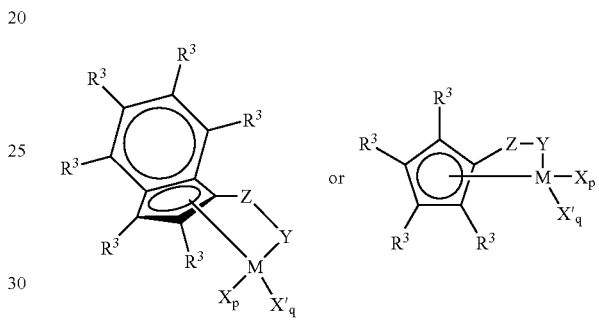

wherein:

$R^3$ independently each occurrence is a group selected from hydrogen, hydrocarbyl, halohydrocarbyl, silyl, germyl and mixtures thereof, said group containing up to 20 nonhydrogen atoms;

M is titanium, zirconium or hafnium;

Z, Y, X and X' are as previously defined;

p is 0, 1 or 2; and q is zero or one;

with the proviso that:

when p is 2, q is zero, M is in the +4 formal oxidation state, and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms, when p is 1, q is zero, M is in the +3 formal oxidation state, and X is a stabilizing anionic ligand group selected from the group consisting of allyl, 2-(N,N-dimethylaminomethyl)phenyl, and 2-(N,N-dimethyl)-aminobenzyl, or M is in the +4 formal oxidation state, and X is a divalent derivative of a conjugated diene, M and X together forming a metallocyclopentene group, and when p is 0, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

More preferred coordination complexes used according to the present invention are complexes corresponding to the formula:

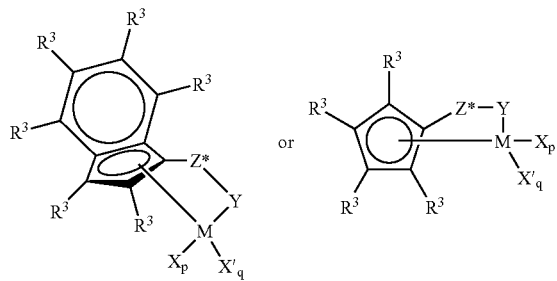

wherein:

R³ independently each occurrence is hydrogen or $C_{1-6}$ alkyl;

M is titanium;

Y is —O—, —S—, —NR*—, —PR*—;

Z* is $SiR^*_2$, $CR^*_2$, $SiR^*_2SiR^*_2$, $CR^*_2CR^*_2$, CR*=CR*, $CR^*_2SiR^*_2$, or $GeR^*_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

p is 0, 1 or 2;

q is zero or one;

with the proviso that:

when p is 2, q is zero, M is in the +4 formal oxidation state, and X is independently each occurrence methyl or benzyl, when p is 1, q is zero, M is in the +3 formal oxidation state, and X is 2-(N,N-dimethyl)aminobenzyl; or M is in the +4 formal oxidation state and X is 2-butene-1,4-diyl, and when p is 0, q is 1, M is in the +2 formal oxidation state, and X' is 1,4-diphenyl-1,3-butadiene or 1,3-pentadiene. The latter diene is illustrative of unsymetrical diene groups that result in production of metal complexes that are actually mixtures of the respective geometrical isomers.

The complexes can be prepared by use of well known synthetic techniques. A preferred process for preparing the metal complexes is disclosed in U.S. Ser. No. 8/427,378, filed Apr. 24, 1995, now U.S. Pat. No. 5,491,246 the teachings of which are hereby incorporated by reference. The reactions are conducted in a suitable noninterfering solvent at a temperature from −100 to 300° C., preferably from −78 to 100° C., most preferably from 0 to 50° C. A reducing agent may be used to cause the metal M, to be reduced from a higher to a lower oxidation state. Examples of suitable reducing agents are alkali metals, alkaline earth metals, aluminum and zinc, alloys of alkali metals or alkaline earth metals such as sodium/mercury amalgam and sodium/potassium alloy, sodium naphthalenide, potassium graphite, lithium alkyls, lithium or potassium alkadienyls, and Grignard reagents.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

In the preferred catalyst systems to be used in the present invention, the active species of the catalyst is strongly associated with a carrier, so that the active species of the catalyst is not liberated from the carrier and does not escape from the polymer being produced.

(b) The Solid Component

Specifically stated, in one preferred supported catalyst component to be used in the process of the present invention, an active hydrogen moiety of an activator compound for the transition metal component, may be bonded to the hydroxyl groups of the support material through an organometal compound. That is, the activator compound is strongly associated with the support material. Such supported catalyst components are more fully described in WO 96/28480 the teachings of which contained therein, are herein incorporated in their entirety by reference In a further preferred supported catalyst component to be used in the present invention aluminoxane is fixed to the support material by a heating and/or washing treatment, such that the aluminoxane is substantially not extractable under severe conditions (toluene at 90° C.). Such supported catalyst components are more fully described in WO 96/16092, the teachings of which contained therein, are herein incorporated in their entirety by reference Suitable support materials for use in the present invention include porous resinous materials, for example, polyolefins such as polyethylenes and polypropylenes or copolymers of styrene-divinylbenzene, and solid inorganic oxides including oxides of Group 2, 3, 4, 13, or 14 metals, such as silica, alumina, magnesium oxide, titanium oxide, thorium oxide, as well as mixed oxides of silica. Suitable mixed oxides of silica include those of silica and one or more Group 2 or 13 metal oxides, such as silica-magnesia or silica-alumina mixed oxides. Silica, alumina, and mixed oxides of silica and one or more Group 2 or 13 metal oxides are preferred support materials. Preferred examples of such mixed oxides are the silica-aluminas. The most preferred support material is silica. The shape of the silica particles is not critical and the silica may be in granular, spherical, agglomerated, fumed or other form. Suitable silicas include those that are available from Grace Davison (division of W.R. Grace & Co.) under the designations SD 3216.30, SP-9-10046, Davison Syloid™ 245, Davison 948 and Davison 952, from Degussa AG under the designation Aerosil 812, and from Crossfield under the designation ES 70x.

Support materials suitable for the present invention preferably have a surface area as determined by nitrogen porosimetry using the B.E.T. method from 10 to about 1000 m²/g, and preferably from about 100 to 600 m²/g. The pore volume of the support, as determined by nitrogen adsorption, is typically up to 5 cm³/g, advantageously between 0.1 and 3 cm³/g, preferably from about 0.2 to 2 cm³/g. The average particle size is not critical but typically is from 0.5 to 500 μm, preferably from 1 to 200 μm, more preferably to 100 μm.

The support material may be subjected to a heat treatment and/or chemical treatment to reduce the water content or the hydroxyl content of the support material. Both dehydrated support materials and support materials containing small amounts of water can be used. Typical thermal pretreatments are carried out at a temperature from 30° C. to 1000° C. for a duration of 10 minutes to 50 hours in an inert atmosphere or under reduced pressure. Typical support materials have a surface hydroxyl content of from 0.1 micromol, preferably from 5 micromol, more preferably from 0.05 mmol to not more than 10 mmol and preferably not more than 5 mmol hydroxyl groups per g of solid support, more preferably from 0.5 to 2 mmol per gram. The hydroxyl content can be determined by known techniques, such as infrared spectroscopy and titration techniques using a metal alkyl or metal hydroxide, for example, adding an excess of dialkyl magnesium to a slurry of the solid support and determining the amount of dialkyl magnesium remaining in solution via known techniques. This latter method is based on the reaction of S—OH+ MgR$_2$→S—OMgR+RH, wherein S is the solid support.

As an alternative technique for measuring the amount of hydroxyl groups on the surface of the inorganic solid, a method comprising the following procedures can be mentioned. Illustratively stated, the inorganic solid is dried in a nitrogen gas flow at 250° C. for 10 hours and then, the weight of the dried inorganic solid is measured and taken as an initial weight represented by "W1" (unit: g). After this, the dried inorganic solid is heated to 1,000° C. and then, allowed to cool to the room temperature. The weight of the cooled inorganic solid is measured, and the difference between the initial weight (W1) and the weight of the cooled inorganic solid is determined and taken as a weight loss represented by "ΔW" (unit: g). The amount of the hydroxyl groups is calculated by the following formula:

Amount of the hydroxyl groups=(1,000×ΔW/18.02)/W1 mmol/g.

It is preferred that the inorganic solid having hydroxyl groups on the surface thereof to be used in the method of the present invention do not contain water such as crystal water or adsorbed water. Any water contained in the inorganic solid can be removed therefrom by heating in a nitrogen atmosphere or under reduced pressure at 250° C. or more for 1 hour or more.

According to one preferred embodiment, the solid (or supported) catalyst comprises a supported catalyst component comprising (a) a support material, an organometal compound wherein the metal is selected from Groups 2-13 of the Periodic Table of the Elements, germanium, tin, and lead, and (b) an activator compound comprising (b-1) a cation which is capable of reacting with a transition metal compound to form a catalytically active transition metal complex, and (b-2) a compatible anion having up to 100 nonhydrogen atoms and containing at least one substituent comprising an active hydrogen moiety; and a transition metal compound.

The support material is typically treated with the organometal compound. Suitable organometal compounds are those comprising metals of Groups 2-13, germanium, tin, and lead, and at least two substituents selected from hydride, hydrocarbyl radicals, trihydrocarbyl silyl radicals, and trihydrocarbyl germyl radicals. Additional substituents preferably comprise one or more substituents selected from hydride, hydrocarbyl radicals, trihydrocarbyl substituted silyl radicals, trihydrocarbyl substituted germyl radicals, and hydrocarbyl-, trihydrocarbyl silyl- or trihydrocarbyl germyl-substituted metalloid radicals.

The recitation "metalloid", as used herein, includes non-metals such as boron, phosphorus and the like which exhibit semi-metallic characteristics.

Examples of such organometal compounds include organomagnesium, organozinc, organoboron, organoaluminum, organogermanium, organotin, and organolead compounds, and mixtures thereof. Further suitable organometal compounds are alumoxanes. Preferred examples are alumoxanes and compounds represented by the following formulae: MgR$^1_2$, ZnR$^1_2$, BR$^1_x$R$^2_y$, AlR$^1_x$R$^2_y$, wherein R$^1$ independently each occurrence is hydride, a hydrocarbyl radical, a trihydrocarbyl silyl radical, a trihydrocarbyl germyl radical, or a trihydrocarbyl-, trihydrocarbyl silyl-, or trihydrocarbyl germyl-substituted metalloid radical, R$^2$ independently is the same as R$^1$, x is 2 or 3, y is 0 or 1 and the sum of x and y is 3, and mixtures thereof. Examples of suitable hydrocarbyl moieties are those having from 1 to 20 carbon atoms in the hydrocarbyl portion thereof, such as alkyl, aryl, alkaryl, or aralkyl. Preferred radicals include methyl, ethyl, n- or i-propyl, n-, s- or t-butyl, phenyl, and benzyl. Preferably, the aluminum component is selected from the group consisting of alumoxane and aluminum compounds of the formula AlR$^1_x$ wherein R$^1$ in each occurrence independently is hydride or a hydrocarbyl radical having from 1 to 20 carbon atoms, and x is 3. Suitable trihydrocarbyl aluminum compounds are trialkyl or triaryl aluminum compounds wherein each alkyl or aryl group has from 1 to 10 carbon atoms, or mixtures thereof, and preferably trialkyl aluminum compounds such as trimethyl, triethyl, tri-isobutyl aluminum.

Alumoxanes (also referred to as aluminoxanes) are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae (—Al(R)—O)$_m$, for a cyclic alumoxane, and R$_2$Al—O(—Al(R)—O)$_m$—AlR$_2$, for a linear compound, wherein R independently in each occurrence is a C$_1$-C$_{10}$ hydrocarbyl, preferably alkyl, or halide and m is an integer ranging from 1 to about 50, preferably at least about 4. Alumoxanes are typically the reaction products of water and an aluminum alkyl, which in addition to an alkyl group may contain halide or alkoxide groups. Reacting several different aluminum alkyl compounds, such as, for example, trimethyl aluminum and tri-isobutyl aluminum, with water yields so-called modified or mixed alumoxanes. Preferred alumoxanes are methylalumoxane and methylalumoxane modified with minor amounts of other lower alkyl groups such as isobutyl. Alumoxanes generally contain minor to substantial amounts of starting aluminum alkyl compound.

The way in which the alumoxane is prepared is not critical. When prepared by the reaction between water and aluminum alkyl, the water may be combined with the aluminum alkyl in various forms, such as liquid, vapor, or solid, for example in the form of crystallization water. Particular techniques for the preparation of alumoxane type compounds by contacting an aluminum alkyl compound with an inorganic salt containing water of crystallization are disclosed in U.S. Pat. No. 4,542,199. In a particular preferred embodiment an aluminum alkyl compound is contacted with a regeneratable water-containing substance such as hydrated alumina, silica or other substance. This is disclosed in European Patent Application No. 338,044, incorporated herein by reference.

The supported catalyst according to this embodiment generally comprise a support material combined or treated with the organometal compound and containing at least 0.1 micromol of organometal compound per g of support material, typically at least 5 micromole per g support material, advantageously at least 0.5 weight percent of the metal, preferably aluminum, expressed in gram of metal atoms per g of support material. Preferably, the amount of metal is at least 2 weight percent, and generally not more than 40 weight percent, and more preferably not more than 30 weight percent. At too high amounts of metal the supported catalyst becomes expensive. At too low amounts the catalyst efficiency goes down to drop below acceptable levels.

The supported catalyst preferably contain a treated support material (a) comprising a support material and an alumoxane wherein not more than about 10 percent aluminum present in the treated support material is extractable in a one hour extraction with toluene of 90° C. using about 10 mL toluene per gram of pretreated support material. More preferably, not more than about 9 percent aluminum present in the supported catalyst component is extractable, and most preferably not more than about 8 percent. This is especially advantageous when the supported catalyst is used in a polymerization process where a diluent or solvent is used which may extract non-fixed alumoxane from the support material. It has been found that when the amount of extractables is below the levels given above, the amount of alumoxane that can diffuse into the polymerization solvent or diluent, if used, is so low that no appreciable amount of polymer will be formed in the diluent, as compared to polymer formed on the support material. If too much polymer is formed in the diluent the polymer bulk density will decrease below acceptable levels and reactor fouling problems may occur.

The toluene extraction test is carried out as follows: About 1 g of supported catalyst component or supported catalyst, with a known aluminum content, is added to 10 mL toluene and the mixture is then heated to 90° C. under an inert atmosphere. The suspension is stirred well at this temperature for 1 hour. Then the suspension is filtered applying reduced pressure to assist in the filtration step. The solids are washed twice with about 3 to 5 mL toluene of 90° C. per gram of solids. The solids are then dried at 120° C. for 1 hour, and subsequently the aluminum content of the solids is measured. The difference between the initial aluminum content and the aluminum content after the extraction divided by the initial aluminum content and multiplied by 100%, gives the amount of extractable aluminum.

The aluminum content can be determined by slurrying about 0.5 g of supported catalyst component or supported catalyst in 10 mL hexane. The slurry is treated with 10 to 15 mL 6N sulfuric acid, followed by addition of a known excess of EDTA. The excess amount of EDTA is then back-titrated with zinc chloride.

Without wishing to be bound by any theory, it is believed that the activator compound according to this embodiment reacts with the organometal compound through the active hydrogen-containing substituent. It is believed that a group $R^1$ of the organometal compound combines with the active hydrogen moiety of the activator compound to release a neutral organic compound, for example an alkane, or hydrogen gas thereby chemically coupling the metal atom with the activator compound residue. Thus the activator is believed to become chemically attached to the support material once the support material has been treated with the organometal compound or adduct of organometal compound and activator compound. Upon addition of the transition metal compound a supported catalyst is formed having improved properties.

The activator compound useful in the present invention contains a compatible anion having up to 100, and preferably up to 50 nonhydrogen atoms and having at least one substituent comprising an active hydrogen moiety. Preferred substituents comprising an active hydrogen moiety correspond to the formula (I):

$$G_q(T\text{-}H)_r \quad \quad (I)$$

wherein G is a polyvalent hydrocarbon radical, T is O, S, NR, or PR, wherein R is a hydrocarbyl radical, a trihydrocarbyl silyl radical, a trihydrocarbyl germyl radical, or hydrogen, H is hydrogen, q is 0 or 1, and preferably 1, and r is an integer from 1 to 3, preferably 1. Polyvalent hydrocarbon radical G has r+1 valencies, one valency being with a metal or metalloid of the Groups 5-15 of the Periodic Table of the Elements in the compatible anion, the other valency or valencies of G being attached to r groups T-H. Preferred examples of G include divalent hydrocarbon radicals such as: alkylene, arylene, aralkylene, or alkarylene radicals containing from 1 to 20 carbon atoms, more preferably from 2 to 12 carbon atoms. Suitable examples of G include phenylene, biphenylene, naphthylene, methylene, ethylene, 1,3-propylene, 1,4-butylene, phenylmethylene (—$C_6H_4$—$CH_2$—). The polyvalent hydrocarbyl portion G may be further substituted with radicals that do not interfere with the coupling function of the active hydrogen moiety. Preferred examples of such non-interfering substituents are alkyl, aryl, alkyl- or aryl-substituted silyl and germyl radicals, and fluoro substituents.

The group T-H in the previous formula thus may be an —OH, —SH, —NRH, or —PRH group, wherein R preferably is a $C_{1-18}$, preferably a $C_{1-10}$ hydrocarbyl radical or hydrogen, and H is hydrogen. Preferred R groups are alkyls, cycloalkyls, aryls, arylalkyls, or alkylaryls of 1 to 18 carbon atoms, more preferably those of 1 to 12 carbon atoms. The —OH, —SH, —NRH, or —PRH groups may be part of a larger functionality such as, for example, C(O)—OH, C(S)—SH, C(O)—NRH, and C(O)—PRH. Most preferably, the group T-H is a hydroxy group, —OH, or an amino group, —NRH.

Very preferred substituents $G_q(T\text{-}H)_r$ comprising an active hydrogen moiety include hydroxy- and amino-substituted aryl, aralkyl, alkaryl or alkyl groups, and most preferred are the hydroxyphenyls, especially the 3- and 4-hydroxyphenyl groups, hydroxytolyls, hydroxy benzyls (hydroxymethylphenyl), hydroxybiphenyls, hydroxynaphthyls, hydroxycyclohexyls, hydroxymethyls, and hydroxypropyls, and the corresponding amino-substituted groups, especially those substituted with —NRH wherein R is an alkyl or aryl radical having from 1 to 10 carbon atoms, such as for example methyl, ethyl, propyl, i-propyl, n-, i-, or t-butyl, pentyl, hexyl, heptyl, octyl, nonyl, and decyl, phenyl, benzyl, tolyl, xylyl, naphthyl, and biphenyl.

The compatible anion containing the substituent which contains an active hydrogen moiety, may further comprise a single Group 5-15 element or a plurality of Group 5-15 elements, but is preferably a single coordination complex comprising a charge-bearing metal or metalloid core, which anion is bulky. A compatible anion specifically refers to an anion which when functioning as a charge balancing anion in the catalyst system of this invention, does not transfer an anionic substituent or fragment thereof to the transition metal cation thereby forming a neutral transition metal compound and a neutral metal by-product. "Compatible anions" are anions which are not degraded to neutrality when the initially formed complex decomposes and are noninterfering with desired subsequent polymerizations.

Preferred anions are those containing a single coordination complex comprising a charge-bearing metal or metalloid core carrying a substituent containing an active hydrogen moiety which anion is relatively large (bulky), capable of stabilizing the active catalyst species (the transition metal cation) which is formed when the activator compound and transition metal compound are combined and said anion will be sufficiently labile to be displaced by olefinic, diolefinic and acetylenically unsaturated compounds or other neutral Lewis bases such as ethers, nitrites and the like. Suitable metals for the anions of activator compounds include, but are not limited to, aluminum, gold, platinum and the like. Suitable metalloids include, but are not limited to, boron, phosphorus, silicon and the like. Activator compounds which contain anions comprising a coordination complex containing a single boron atom and a substituent comprising an active hydrogen moiety are preferred.

Preferably, compatible anions containing a substituent comprising an active hydrogen moiety may be represented by the following general formula (II):

$$[M'^{m+}Q_n(G_q(T-H)_r)_z]^{d-} \quad (II)$$

wherein:

M' is a metal or metalloid selected from Groups 5-15 of the Periodic Table of the Elements;

Q independently in each occurrence is selected from the group consisting of hydride, dihydrocarbylamido, preferably dialkylamido, halide, hydrocarbyloxide, preferably alkoxide and aryloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion having from 1 to 20 carbons with the proviso that in not more than one occurrence is Q halide;

G is a polyvalent hydrocarbon radical having r+1 valencies and preferably divalent hydrocarbon radical bonded to M' and T;

T is O, S, NR, or PR, wherein R is a hydrocarbon radical, a trihydrocarbyl silyl radical, a trihydrocarbyl germyl radical, or hydrogen;

m is an integer from 1 to 7, preferably 3;
n is an integer from 0 to 7, preferably 3;
q is an integer 0 or 1, preferably 1;
r is an integer from 1 to 3, preferably 1;
z is an integer from 1 to 8, preferably 1;
d is an integer from 1 to 7, preferably 1; and
n+z−m=d.

Preferred boron-containing anions which are particularly useful in this invention may be represented by the following general formula (III):

$$[BQ_{4-z'}(G_q(T-H)_r)_{z'}]^{d-} \quad (III)$$

wherein:

B is boron in a valence state of 3;
z' is an integer from 1-4, preferably 1;
d is 1; and
Q, G, T, H, q, and r are as defined for formula (II). Preferably, z' is 1, q is 1, and r is 1.

Illustrative, but not limiting, examples of anions of activator compounds to be used in the present invention are boron-containing anions such as triphenyl(hydroxyphenyl)borate, diphenyl-di(hydroxyphenyl)borate, triphenyl(2,4-dihydroxyphenyl)borate, tri(p-tolyl)-(hydroxyphenyl)borate, tris(pentafluorophenyl)(hydroxyphenyl)borate, tris-(2,4-dimethylphenyl)(hydroxyphenyl)borate, tris-(3,5-dimethylphenyl)(hydroxyphenyl)borate, tris-(3,5-di-trifluoromethylphenyl)(hydroxyphenyl)borate, tris(pentafluorophenyl)(2-hydroxyethyl) borate, tris(pentafluorophenyl)(4-hydroxybutyl)borate, tris(pentafluorophenyl)(4-hydroxycyclohexyl)borate, tris(pentafluorophenyl)(4-(4'-hydroxyphenyl)phenyl)borate, tris(pentafluorophenyl)(6-hydroxy-2-naphthyl)borate, and the like. A highly preferred activator complex is tris(pentafluorophenyl)(4-hydroxyphenyl)borate. Other preferred anions of activator compounds are those above mentioned borates wherein the hydroxy functionality is replaced by an amino NHR functionality wherein R preferably is methyl, ethyl, or t-butyl.

The cationic portion (b-1) of the activator compound to be used in association with the compatible anion (b-2) can be any cation which is capable of reacting with the transition metal compound to form a catalytically active transition metal complex, especially a cationic transition metal complex. The cations (b-1) and the anions (b-2) are used in such ratios as to give a neutral activator compound. Preferably the cation is selected from the group comprising Brønsted acidic cations, carbonium cations, silylium cations, and cationic oxidizing agents.

Brønsted acidic cations may be represented by the following general formula:

$$(L-H)^+$$

wherein:

L is a neutral Lewis base, preferably a nitrogen, phosphorus, or sulfur containing Lewis base; and $(L-H)^+$ is a Brønsted acid. The Brønsted acidic cations are believed to react with the transition metal compound by transfer of a proton of said cation, which proton combines with one of the ligands on the transition metal compound to release a neutral compound.

Illustrative, but not limiting, examples of Brønsted acidic cations of activator compounds to be used in the present invention are trialkyl-substituted ammonium cations such as triethylammonium, tripropylammonium, tri(n-butyl)ammonium, trimethylammonium, tributylammonium, and tri(n-octyl)ammonium. Also suitable are N,N-dialkylanilinium cations such as N,N-dimethylanilinium, N,N-diethylanilinium, N,N-2,4,6-pentamethylanilinium, N,N-dimethylbenzylammonium and the like; dialkylammonium cations such as di-(i-propyl)-ammonium, dicyclohexylammonium and the like; and triarylphosphonium cations such as triphenylphosphonium, tri(methylphenyl)phosphonium, tri(dimethylphenyl)phosphonium, dimethylsulphonium, diethylsulphonium, and diphenylsulphonium.

A second type of suitable cations corresponds to the formula:

$$\copyright^+$$

wherein $\copyright^+$ is a stable carbonium or silylium ion containing up to 30 nonhydrogen atoms, the cation being capable of reacting with a substituent of the transition metal compound and converting it into a catalytically active transition metal complex, especially a cationic transition metal complex. Suitable examples of cations include tropyllium, triphenylmethylium, benzene(diazonium). Silylium salts have been previously generically disclosed in J. Chem. Soc. Chem. Comm., 1993, 383-384, as well as Lambert, J. B., et. al., Organometallics, 1994, 13, 2430-2443. Preferred silylium cations are triethylsilylium, and trimethylsilylium and ether substituted adducts thereof.

Another suitable type of cation comprises a cationic oxidizing agent represented by the formula:

$$Ox^{e+}$$

wherein $Ox^{e+}$ is a cationic oxidizing agent having a charge of e+, and e is an integer from 1 to 3.

Examples of cationic oxidizing agents include: ferrocenium, hydrocarbyl-substituted ferrocenium, $Ag^+$, and $Pb^{2+}$.

The quantity of activator compound in the supported catalyst component and the supported catalyst is not critical, but typically ranges from 0.1, preferably from 1 to 2,000 micromoles of activator compound per gram of treated support material. Preferably, the supported catalyst or component contains from 10 to 1,000 micromoles of activator compound per gram of treated support material.

Generally, the ratio of moles of activator compound to gramatoms of transition metal in the supported catalyst is from 0.05:1 to 100:1, preferably from 0.5:1 to 20:1 and most preferably from 1:1 to 5:1 mole activator compound per gramatom of transition metal in the supported catalyst. At too low ratios the supported catalyst will not be very active, whereas at too high ratios the catalyst becomes less economic due to the relatively high cost associated with the use of large quantities of activator compound.

The supported catalyst according to this embodiment can be prepared by combining the support material with the organometal compound and the activator compound. The order of addition is not critical. The organometal compound may be either first combined with the support material or with the activator compound, and subsequently the activator compound or the support material may be added. One preferred embodiment comprises treating the support material first with the organometal compound by combining the organometal compound in a suitable solvent, such as a hydrocarbon solvent, with the support material. The temperature, pressure, and contact time for this treatment are not critical, but generally vary from −20° C. to about 150° C., from subatmospheric to 10 bar, more preferably at atmospheric pressure, for 5 minutes to 48 hours. Usually the slurry is agitated. After this treatment the solids are typically separated from the solvent. Any excess of organometal compound could then be removed by techniques known in the art. This method is especially suitable for obtaining support material with relatively low metal loadings.

According to a preferred embodiment, the support material is first subjected to a thermal treatment at 100° C. to 1000° C., preferably at about 200° C. to about 850° C. Typically, this treatment is carried out for about 10 minutes to about 72 hours, preferably from about 0.5 hours to 24 hours. Then the thermally treated support material is combined with the organometal compound, preferably $AlR'_3$ wherein $R'$ has the meaning defined hereinbefore in a suitable diluent or solvent, preferably one in which the organometal compound is soluble. Typical solvents are hydrocarbon solvents having from 5 to 12 carbon atoms, preferably aromatic solvents such as toluene and xylenes, or aliphatic solvents of 6 to 10 carbon atoms, such as hexane, heptane, octane, nonane, decane, and isomers thereof, cycloaliphatic solvents of 6 to 12 carbon atoms such as cyclohexane, or mixtures of any of these.

The support material is combined with the organometal compound at a temperature of −20° C. to 150° C., preferably at 20° C. to 100° C. The contact time is not critical and can vary from 5 minutes to 72 hours, and is preferably from 0.5 hours to 36 hours. Agitation is preferably applied. The thus treated support material is then preferably contacted with the activator compound.

An alternative treatment of the support material, suitable for obtaining alumoxane loadings attached to the support material, involves one or both of the following steps (A) and (B):

(A) heating a support material containing alumoxane under an inert atmosphere for a period and at a temperature sufficient to fix alumoxane to the support material;

(B) subjecting the support material containing alumoxane to one or more wash steps to remove alumoxane not fixed to the support material;

thereby selecting the conditions in heating step A and washing step B so as to form a treated support material wherein not more than about 10 percent aluminum present in the treated support material is extractable in a one hour extraction with toluene of 90° C. using about 10 mL toluene per gram of supported catalyst component. High amounts of alumoxane attached to the support material are obtained using first heating step A, optionally followed by wash step B.

In this process the alumoxane treated support material may be obtained by combining in a diluent an alumoxane with a support material containing from zero to not more than 20 weight percent of water, preferably from zero to not more than 6 weight percent of water, based on the total weight of support material and water. The alumoxane desirably is used in a dissolved form.

Alternatively, the alumoxane pretreated support material may be obtained by combining in a diluent, a support material containing from 0.5 to 50 weight percent water, preferably from 1 to 20 weight percent water, based on the total weight of support material and water, with a compound of the formula $R''_{n*}AlX''_{3-n*}$ wherein $R''$ in independently each occurrence is a hydrocarbyl radical, $X''$ is halogen or hydrocarbyloxy, and $n*$ is an integer from 1 to 3. Preferably, $n*$ is 3. $R''$ in independently each occurrence is preferably an alkyl radical, advantageously one containing from 1 to 12 carbon atoms. Preferred alkyl radicals are methyl, ethyl, propyl, isopropyl, n-butyl, isobutyl, tert-butyl, pentyl, iso-pentyl, hexyl, iso-hexyl, heptyl, octyl, and cyclohexyl. Highly preferred compounds of formula $R''_{n*}AlX''_{3-n*}$ are trimethylaluminum, triethylaluminum and tri-isobutylaluminum. When the alumoxane is prepared in situ by reacting the compound of the formula $R''_{n*}AlX''_{3-n*}$ with water, the mole ratio of $R''_{n*}AlX''_{3-n*}$ to water is typically 10:1 to 1:1, preferably from 5:1 to 1:1.

The support material is added to the alumoxane or compound of the formula $R''_{n*}AlX''_{3-n*}$, preferably dissolved in a solvent, most preferably a hydrocarbon solvent, or the solution of alumoxane or compound of the formula $R''_{n*}AlX''_{3-n}*$ is added to the support material. The support material can be used as such in dry form or slurried in a hydrocarbon diluent. Both aliphatic and aromatic hydrocarbons can be used. Suitable aliphatic hydrocarbons include, for example, pentane, isopentane, hexane, heptane, octane, iso-octane, nonane, isononane, decane, cyclohexane, methyl-cyclohexane and combinations of two or more of such diluents. Suitable examples of aromatic diluents are benzene, toluene, xylene, and other alkyl or halogen-substituted aromatic compounds. Most preferably, the diluent is an aromatic hydrocarbon, especially toluene. Suitable concentrations of solid support in the hydrocarbon medium range from about 0.1 to about 15, preferably from about 0.5 to about 10, more preferably from about 1 to about 7 weight percent. The contact time and temperature are not critical. Preferably the temperature is from 0° C. to 60° C., more preferably from 10° C. to 40° C. The contact time is from 15 minutes to 40 hours, preferably from 1 to 20 hours.

Before subjecting the alumoxane-treated support material to the heating step or washing step, the diluent or solvent is preferably removed to obtain a free flowing powder. This is preferably done by applying a technique which only removes the liquid and leaves the aluminum compounds on the solids, such as by applying heat, reduced pressure, evaporation, or a combination thereof. If desired, the removal of diluent can be combined with the heating step, although care should be taken that the diluent is removed gradually.

The heating step and/or the washing step are conducted in such a way that a very large proportion (more than about 90 percent by weight) of the alumoxane which remains on the support material is fixed. Preferably, a heating step is used, more preferably a heating step is used followed by a washing step. When used in the preferred combination both steps cooperate such that in the heating step the alumoxane is fixed to the support material, whereas in the washing step the alumoxane which is not fixed is removed to a substantial degree. The upper temperature for the heat-treatment is preferably below the temperature at which the support material begins to agglomerate and form lumps which are difficult to redisperse, and below the alumoxane decomposition temperature. When the transition metal compound c) is added before the heat treatment, the heating temperature should be below the decomposition temperature of the transition metal compound. Preferably, the heat-treatment is carried out at a temperature from 75° C. to 250° C. for a period from 15 minutes to 24 hours. More preferably, the heat treatment is carried out at a temperature from 160° C. to 200° C. for a period from 30 minutes to 4 hours. Good results have been obtained while heating for 8 hours at 100° C. as well as while heating for 2 hours at 175° C. By means of preliminary experiments, a person skilled in the art will be able to define the heat-treatment conditions that will provide the desired result. It is also noted, that the longer the heat treatment takes, the higher the amount of alumoxane fixed to the support material will be. The heat-treatment is carried out at reduced pressure or under an inert atmosphere, such as nitrogen gas, or both but preferably at reduced pressure. Depending on the conditions in the heating step, the alumoxane may be fixed to the support material to such a high degree that a wash step may be omitted.

In the wash step, the number of washes and the solvent used are such that sufficient amounts of non-fixed alumoxane are removed. The washing conditions should be such that non-fixed alumoxane is soluble in the wash solvent. The support material containing alumoxane, preferably already subjected to a heat-treatment, is preferably subjected to one to five wash steps using an aromatic hydrocarbon solvent at a temperature from 0° C. to 110° C. More preferably, the temperature is from 20° C. to 100° C. Preferred examples of aromatic solvents include toluene, benzene and xylenes. More preferably, the aromatic hydrocarbon solvent is toluene. At the end of the wash treatment, the solvent is removed by a technique that also removes the alumoxane dissolved in the solvent, such as by filtration or decantation. Preferably, the wash solvent is removed to provide a free flowing powder.

The organometal compound treated support material is then typically reslurried in a suitable diluent and combined with the activator compound. The activator compound is preferably used in a diluent. Suitable diluents include hydrocarbon and halogenated hydrocarbon diluents. Any type of solvent or diluent can be used which does not react with the catalyst components in such a way as to negatively impact the catalytic properties. Preferred diluents are aromatic hydrocarbons, such as toluene, benzene, and xylenes, and aliphatic hydrocarbons such as hexane, heptane, and cyclohexane. Preferred halogenated hydrocarbons include methylene chloride and carbon tetrachloride. The temperature is not critical but generally varies between −20° C. and the decomposition temperature of the activator. Typical contact times vary from a few minutes to several days. Agitation of the reaction mixture is preferred. Advantageously, the activator compound is dissolved, using heat to assist in dissolution where desired. It may be desirable to carry out the contacting between the organometal-treated support material and the activator compound at elevated temperatures. Preferably, such elevated temperatures are from 45° C. to 120° C.

Instead of first treating the support material with the organometal compound, preferably aluminum component, and subsequently adding the activator compound, the organometal compound, preferably aluminum component, and activator compound may be combined in a suitable diluent prior to adding or combining the reaction mixture to or with the thermally treated support material or the support material containing from 0.5 to 50 weight percent water.

Without wishing to be bound by any theory, it is believed that an organo group of the organometal compound reacts with the active hydrogen moiety contained in the activator anion (b-2) to form a reaction or contact product (hereinafter also referred to as "adduct"). For example, when the organometal compound is trialkylaluminum $AlR_3$ and the active hydrogen-containing moiety is represented by G-OH, the reaction product is believed to comprise $G-O-AlR_2$ whereas further an alkane by-product RH is formed. This adduct G-O-$AlR_2$ when combined with the support material containing hydroxyl groups, Si—OH in case of a silica support material, is believed to form Si—O—Al(R)—O-G together with alkane RH as by-product. This method of preparing the supported catalyst component has been found to run very smoothly and to provide catalysts and catalyst precursors or components having desirable properties. Typical ratios to be used in this reaction are from about 1:1 to about 20:1 moles of organometal compound to mole equivalents of active hydrogen moieties contained in the activator anion (b-2).

The amount of adduct, formed by combining the organometal compound with the activator compound, to be combined with the support material is not critical. Preferably, the amount is not higher than can be fixed to the support material. Typically, this is determined by the amount of support material hydroxyls. The amount of adduct to be employed is preferably not more than the equivalent amount of such hydroxyl groups. Less than the equivalent amount is preferably used, more preferably the ratio between moles of adduct to moles of surface reactive groups such as hydroxyls is between 0.01 and 1, even more preferably between 0.02 and 0.8. Prior to adding the transition metal compound it is preferred, especially when less than an equivalent amount of adduct is added with respect to surface reactive groups, to add an additional amount of organometal compound to the reaction product of support material and the adduct to remove any remaining surface reactive groups which otherwise may react with the transition metal and thus require higher amounts thereof to achieve equal catalytic activity. Prior to combining it with the transition metal compound, the supported catalyst component can be washed, if desired, to remove any excess of adduct or organometal compound.

The supported catalyst component comprising the support material, organometal compound, and the activator may be isolated to obtain a free flowing powder by removing the liquid medium using preferably filtration or evaporation techniques.

Although the transition metal compound may be combined with the activator compound, or the adduct of the organometal compound and the activator compound, prior to combining the activator compound or its adduct with the support material, this results in reduced catalyst efficiencies. Preferably, the transition metal is first combined with the support material treated with the organometal component and before adding the activator compound, or the transition metal is added after the treated support material and activator have been combined, or after the activator adduct and the support material have been combined. Most preferably, the transition metal compound (c) is added to the reaction product of the support material treated with the organometal compound and activator compound, or after the activator adduct and the support material have been combined.

The transition metal compound is preferably used dissolved in a suitable solvent, such as a hydrocarbon solvent, advantageously a $C_{5-10}$ aliphatic or cycloaliphatic hydrocarbon or a $C_{6-10}$ aromatic hydrocarbon. The contact temperature is not critical provided it is below the decomposition temperature of the transition metal and of the activator. Good results are obtained in a temperature range of 0° C. to 100° C. All steps in the present process should be conducted in the absence of oxygen and moisture.

Upon combining the transition metal compound with the supported catalyst component, the supernatant liquid typically is colorless indicating that the transition metal compound, which solution typically is colored, substantially remains with the solid supported catalyst.

According to an alternative preferred embodiment the solid (or supported) catalyst comprises:

a supported catalyst component comprising a support material and an alumoxane wherein not more than about 10 percent aluminum present in the supported catalyst component is extractable in a one hour extraction with toluene of 90° C. using about 10 ml toluene per gram of supported catalyst component;

and a transition metal compound.

This solid catalyst according to this embodiment may be used in the absence of the activator compound comprising (b-1) a cation which is capable of reacting with a transition metal compound to form a catalytically active transition metal complex, and (b-2) a compatible anion having up to 100 nonhydrogen atoms and containing at least one substituent comprising an active hydrogen moiety.

According to this alternative embodiment, the aluminum atom (from the alumoxane component) to transition metal atom mole ratio in the supported catalyst generally is from 1 to 5000, preferably from 25 to 1000 and most preferably from 50 to 500.

The quantity of transition metal compound in the supported catalyst of the present invention is not critical, but typically ranges from 0.1 to 1000 micromoles of transition metal compound per gram of support material. Preferably, the supported catalyst contains from 1 to 250 micromoles of transition metal compound per gram of support material.

The supported catalyst according to this embodiment is obtainable by heating and/or washing a support material containing alumoxane under an inert atmosphere for a period and at a temperature sufficient to fix alumoxane to the support material, as discussed above.

It may be advantageous to use in the present process the solid catalyst in association with impurity scavengers which serve to protect the solid catalyst from catalyst poisons such as water, oxygen, and polar compounds. Preferred compounds for this purpose include an organoaluminum compound represented by the following formula:

wherein R is a $C_1$-$C_{20}$ hydrocarbyl group; X is a halogen atom or a $C_1$-$C_{20}$ hydrocarbyloxy group; and n is a positive integer selected from 1 to 3, or an organoaluminumoxy compound represented by the following formula:

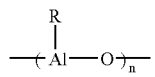

wherein R is a $C_1$-$C_{20}$ hydrocarbyl group; and n is a positive integer selected from 5 to 50.

By the treatment with the organoaluminum compound or the organoaluminumoxy compound, the resistance of the solid catalyst system to impurities, such as water, oxygen and the like which are present in the solid catalyst system, can be improved, and the solid catalyst system can be stored for a prolonged period of time.

In the above treatment, the organoaluminum compound or the organoaluminumoxy compound is used preferably in an amount of 0.1 to 100 mol in terms of aluminum, more preferably in an amount of 1 to 30 mol, per mol of a transition metal compound contained in the solid catalyst system. It is noted that the organoaluminiumoxy compound should preferably not be used in amount that may cause desorption of the transition metal compound from the solid catalyst. The solid catalyst system to be used in the method of the present invention can be stored in the form of a slurry thereof in an inert hydrocarbon solvent, or dried and stored in a solid form thereof.

The polymerization conditions for manufacturing the higher density ethylene homopolymer of the present invention are generally those useful in the slurry polymerization process, although gas phase polymerization processes are also believed to be useful, provided the proper catalysts and polymerization conditions are employed. A description of the slurry process can be found in Volume 6 of the "Encyclopedia of Polymer Science and Engineering" (John Wiley and Sons) pages 472 to 477.

By conducting the slurry polymerization under appropriately controlled reaction conditions, the ethylene copolymer being formed around the solid catalyst system is not melted or dissolved during the polymerization reaction, but maintains a powdery form (which powdery form is achieved by the use of the above-mentioned specific catalyst system) during the reaction.

When a polymerization reaction is conducted under slurry process conditions, the polymerization pressure is generally from 1 to 100 atm, preferably from 3 to 30 atm, and the polymerization temperature is generally from 20 to 115° C., preferably from 50 to 105° C. However, the upper limit of the polymerization temperature is a temperature which is highest among temperatures at which the ethylene copolymer produced can maintain substantially a powdery state. This temperature varies depending on the density of the ethylene copolymer produced and the type of diluent used.

As a diluent to be used for slurry polymerization, typical inert aliphatic or aromatic hydrocarbon solvents can be suitably used, including xylene, benzene, toluene, isobutane, isopentane, heptane, hexane and octane. Hexane, isobutane and isopentane are especially preferred.

In producing the higher density ethylene homopolymer, the molecular weight can be controlled by changing the content of hydrogen in the reaction system or by changing the polymerization temperature, as described in DE 3127133.2, incorporated herein by reference.

In the present invention, the solid catalyst system may contain, in addition to the above-mentioned components, various additives which are known to be useful for ethylene polymerization.

Properties of the Ethylene Homopolymer

The ethylene homopolymers of the present invention have the following unusual combination of properties.

The density satisfies the following inequality;

$$\text{density}(g/cm^3) > 0.9611 + 0.0058 \log (I_2) - 0.00128 \log^2 (I_2)$$

In addition the density is of from about 0.915 to about 0.985, preferably of from about 0.935 to about 0.983, more preferably of from about 0.945 to about 0.980 g/cm³.

The melt index ($I_2$) is of from about 0.0001 to about 10,000, preferably of from about 0.001 to about 5,000, more preferably of from about 0.01 to about 3,000 g/10 min.

The $I_{21}/I_2$ ratio is of from about 15 to about 65, preferably of from about 18 to about 55, more preferably of from about 20 to about 50, or the $I_{10}/I_2$ ratio is of from about 5 to about 30, preferably of from about 5 to about 28, more preferably of from about 5.5 to about 25.

The $M_w/M_n$ ratio (as measured by GPC) greater than about 2.5, preferably from about 2.5 to about 10, more preferably from about 2.8 to about 8, most preferably from about 3 to about 6.

In addition, the $M_w/M_n$ satisfies the following inequalities;

$$M_w/M_n \leq 11.67 \log M_w - 43.67; \text{preferably}$$

$$M_w/M_n \leq 5.15 \log M_w - 11.59; \text{more preferably}$$

$$M_w/M_n \leq 3.50 \log M_w - 11.00; \text{even more preferably}$$

$$1.25 \log M_w - 2.5 \leq M_w/M_n \leq 3.5 \log M_w - 11.0$$

Blend Compositions Comprising the Ethylene Homopolymer.

In addition to the ethylene homopolymer, also included the current invention are blend compositions comprising the ethylene homopolymer (Component A) with various other ethylene interpolymers or homopolymers (Component B).

a) Blend Compositions of the Ethylene Homopolymer with Homogeneous Narrow Composition Distribution Ethylene Interpolymers.

Blends of the ethylene homopolymer with homogeneous narrow composition interpolymers, most preferably the substantially linear ethylene/α-olefin interpolymers are another aspect of the present invention. The homogeneous polymers and interpolymers components of the blend compositions are herein defined as defined in U.S. Pat. No. 3,645,992 (Elston), the disclosure of which is incorporated herein by reference. Accordingly, homogeneous polymers and interpolymers are those in which the comonomer is randomly distributed within a given interpolymer molecule and wherein substantially all of the interpolymer molecules have the same ethylene/comonomer ratio within that interpolymer. Such interpolymers are distinct from the typical Ziegler catalyzed interpolymers which are known as heterogeneous interpolymers and are those in which the interpolymer molecules do not have the same ethylene/comonomer ratio. The homogeneous polymers are also distinct from LDPE produced by high pressure free radical catalyzed ethylene polymerization which results in highly branched polyethylene which is known to those skilled in the art to have numerous long chain branches.

The term "narrow composition distribution" used herein describes the comonomer distribution for homogeneous interpolymers and means that the homogeneous interpolymers have only a single melting peak as measured by Differential Scanning Calorimetry (DSC) and essentially lack a measurable "linear" polymer fraction.

The narrow composition distribution homogeneous interpolymers can also be characterized by their SCBDI (Short Chain Branch Distribution Index) or CDBI (Composition Distribution Branch Index) which is defined as the weight percent of the polymer molecules having a comonomer content within 50 percent of the median total molar comonomer content. The CDBI of a polymer is readily calculated from data obtained from techniques known in the art, such as, for example, temperature rising elution fractionation (abbreviated herein as "TREF") as described, for example, in Wild et al, *Journal of Polymer Science, Poly. Phys. Ed., Vol.* 20, p. 441 (1982), in U.S. Pat. No. 4,798,081 (Hazlitt et al.), or as is described in U.S. Pat. No. 5,008,204 (Stehling), the disclosure of which is incorporated herein by reference. The technique for calculating CDBI is described in U.S. Pat. No. 5,322,728 (Davey et al.) and in U.S. Pat. No. 5,246,783 (Spenadel et al.) or in U.S. Pat. No. 5,089,321 (Chum et al.) the disclosures of all of which are incorporated herein by reference. The SCBDI or CDBI for the homogeneous narrow composition ethylene/α-olefin interpolymers used in the present invention is preferably greater than about 50 percent, especially greater than about 70 percent, most preferably greater than about 90%.

The narrow composition distribution homogeneous interpolymer blend components of this invention essentially lack a measurable "high density" (or homopolymer) fraction as measured by the TREF technique. The homogeneous interpolymers and polymers have a degree of branching less than or equal to 2 methyls/1000 carbons in about 15 percent (by weight) or less, preferably less than about 10 percent (by weight), and especially less than about 5 percent (by weight).

Preferred components of the blends of the current invention are the substantially linear ethylene/α-olefin interpolymers. The substantially linear ethylene/α-olefin interpolymers are herein defined as in U.S. Pat. Nos. 5,272,236 and 5,278,272, the disclosure of which is incorporated herein by reference. The substantially linear ethylene/α-olefin interpolymers are also homogeneous interpolymers as the comonomer is randomly distributed within a given interpolymer molecule and substantially all of the interpolymer molecules have the same ethylene/comonomer ratio within that interpolymer.

However the term "substantially linear" ethylene/α-olefin interpolymer means that the polymer also contains long chain branching. Long chain branching is defined herein as a chain length of at least one carbon more than two carbons less than the total number of carbons in the comonomer, for example, the long chain branch of an ethylene/octene substantially linear ethylene interpolymer is at least seven (7) carbons in length (i.e., 8 carbons less 2 equals 6 carbons plus one equals seven carbons long chain branch length). The long chain branch can be as long as about the same length as the length of the polymer back-bone. Long chain branching is determined by using $^{13}C$ nuclear magnetic resonance (NMR) spectroscopy and is quantified using the method of Randall (*Rev. Macromol. Chem. Phys.*, C29 (2&3), p. 285-297), the disclosure of which is incorporated herein by reference. Long chain branching, of course, is to be distinguished from short chain branches which result solely from incorporation of the comonomer, so for example the short chain branch of an ethylene/octene substantially linear polymer is six carbons in length, while the long chain branch for that same polymer is at least seven carbons in length.

More specifically, the polymer backbone of a substantially linear ethylene/α-olefin interpolymer is substituted with about 0.01 long chain branches/1000 carbons to about 3 long chain branches/1000 carbons, more preferably from about 0.01 long chain branches/1000 carbons to about 1 long chain branches/1000 carbons, and especially from about 0.05 long chain branches/1000 carbons to about 1 long chain branches/1000 carbons.

The substantially linear ethylene/α-olefin interpolymers useful in this invention surprisingly have excellent processability, even though they have relatively narrow molecular weight distributions. The substantially linear ethylene/α-olefin interpolymers have a molecular weight distribution, $M_w/M_n$, defined by the equation:

$$M_w/M_n \leq (I_{10}/I_2) - 4.63.$$

Even more surprising, the melt flow ratio ($I_{10}/I_2$) of the substantially linear olefin polymers can be varied essentially independently of the polydispersity index (i.e., molecular weight distribution ($M_w/M_n$)). This is contrasted with conventional heterogeneously branched linear polyethylene resins having rheological properties such that as the polydispersity index increases, the $I_{10}/I_2$ value also increases.

For the substantially linear ethylene/α-olefin polymers used in the compositions of the invention, the $I_{10}/I_2$ ratio indicates the degree of long chain branching, i.e., the higher the $I_{10}/I_2$ ratio, the more long chain branching in the polymer.

The "rheological processing index" (PI) is the apparent viscosity (in kpoise) of a polymer measured by a gas extrusion rheometer (GER). The gas extrusion rheometer is described by M. Shida, R. N. Shroff and L. V. Cancio in *Polymer Engineering Science, Vol.* 17, no. 11, p. 770 (1977), and in "Rheometers for Molten Plastics" by John Dealy, published by Van Nostrand Reinhold Co. (1982) on page 97-99, both publications of which are incorporated by reference herein in their entirety. All GER experiments are performed at a temperature of 190° C., at nitrogen pressures between 5250 to 500 psig using a 0.0296 inch diameter, 20:1 L/D die with an entrance angle of 180°. For the substantially linear ethylene/α-olefin polymers described herein, the PI is the apparent viscosity (in kpoise) of a material measured by GER at an apparent shear stress of $2.15 \times 10^6$ dyne/cm$^2$. The substantially linear ethylene/α-olefin interpolymers described herein preferably have a PI in the range of about 0.01 kpoise to about 50 kpoise, preferably about 15 kpoise or less. The substantially linear ethylene/α-olefin polymers described herein have a PI less than or equal to about 70 percent of the PI of a comparative linear ethylene/α-olefin polymer which does not contain long chain branching but of about the same $I_2$ and $M_w/M_n$.

An apparent shear stress vs. apparent shear rate plot is used to identify the melt fracture phenomena. According to Ramamurthy in *Journal of Rheology,* 30(2), 337-357, 1986, above a certain critical flow rate, the observed extrudate irregularities may be broadly classified into two main types: surface melt fracture and gross melt fracture.

Surface melt fracture occurs under apparently steady flow conditions and ranges in detail from loss of specular gloss to the more severe form of "sharkskin". In this disclosure, the onset of surface melt fracture (OSMF) is characterized at the beginning of losing extrudate gloss at which the surface roughness of extrudate can only be detected by 40× magnification. The critical shear rate at onset of surface melt fracture for the substantially linear ethylene/α-olefin interpolymers is at least 50 percent greater than the critical shear rate at the onset of surface melt fracture of a linear ethylene/α-olefin polymer which does not contain long chain branching but of about the same $I_2$ and $M_w$/Mn, wherein "about the same" as used herein means that each value is within 10 percent of the comparative value of the comparative linear ethylene polymer.

Gross melt fracture occurs at unsteady flow conditions and ranges in detail from regular (alternating rough and smooth, helical, etc.) to random distortions. For commercial acceptability, (e.g., in blown film products), surface defects should be minimal, if not absent. The critical shear rate at onset of surface melt fracture (OSMF) and onset of gross melt fracture (OGMF) will be used herein based on the changes of surface roughness and configurations of the extrudates extruded by a GER.

The homogeneous interpolymer component of the blend can be an ethylene homopolymer or, preferably, interpolymers of ethylene with at least one comonomer selected from the group consisting of a compound represented by the formula H$_2$C=CHR wherein R is a C$_1$-C$_{18}$ linear, branched or cyclic alkyl group or a C$_6$-C$_{20}$ aryl group, and a C$_4$-C$_{20}$ linear, branched or cyclic diene. Illustrative examples of the compounds represented by the formula H$_2$C=CHR include propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, vinylcyclohexene and styrene. Illustrative examples of C$_4$-C$_{20}$ linear, branched and cyclic dienes include 1,3-butadiene, 1,4-pentadiene, 1,5-hexadiene, 1,4-hexadiene and cyclo hexadiene. Of these, propylene, 1-butene, 1-pentene, 1-hexene, 4-methyl-1-pentene, 1-octene, 1-decene, 1-dodecene, 1-tetradecene, 1-hexadecene, 1-octadecene and 1-eicosene are especially preferred.

The homogeneous narrow composition distribution ethylene/α-olefin interpolymer component may be prepared using the previously described single site catalysts. Preparation of the homogeneous narrow composition distribution substantially linear ethylene/α-olefin polymers requires the use of the previously described constrained geometry single site catalysts.

Suitable activating cocatalysts useful in combination with the single site catalyst component are those compounds capable of abstraction of an X substituent therefrom to form an inert, noninterfering counter ion, or that form a zwitterionic derivative of the catalyst component. Suitable activating cocatalysts for use herein include perfluorinated tri(aryl)boron compounds, and most especially tris(pentafluoro-phenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, and ferrocenium salts of compatible, noncoordinating anions. Suitable activating techniques include the use of bulk electrolysis. A combination of the foregoing activating cocatalysts and techniques may be employed as well. The foregoing activating cocatalysts and activating techniques have been previously taught with respect to different metal complexes in the following references: European Patent EP-A-277,003, U.S. Pat. No. 5,153,157, U.S. Pat. No. 5,064,802, European Patents EP-A-468,651 and EP-A-520,732 (equivalent to U.S. Ser. No. 07/876,268 filed May 1, 1992 now U.S. Pat. No. 5,625,087), and U.S. Pat. No. 5,350,723, the teachings of which are hereby incorporated by reference.

More particularly, suitable ion forming compounds useful as cocatalysts comprise a cation which is a Brønsted acid capable of donating a proton, and a compatible, noncoordinating anion, A$^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron, atom in the anion portion, are available commercially.

Preferably such cocatalysts may be represented by the following general formula:

$$(L^*-H)^+_d(A)^{d-}$$

wherein:
L* is a neutral Lewis base;
$(L^*-H)^+$ is a Bronsted acid;
$A^{d-}$ is a noncoordinating, compatible anion having a charge of d−, and
d is an integer from 1 to 3.

More preferably $A^{d-}$ corresponds to the formula: $[M'Q_4]^-$;
wherein:
M' is boron or aluminum in the +3 formal oxidation state; and
Q independently each occurrence is selected from hydride, dialkylamido, halide, hydrocarbyl, hydrocarbyloxide, halo-substituted-hydrocarbyl, halosubstituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred example, d is one, that is, the counter ion has a single negative charge and is $A^-$. Activating cocatalysts comprising boron which are particularly useful in the preparation of catalysts of this invention may be represented by the following general formula:

$$(L^*-H)^+(BQ_4)^-;$$

wherein:
L* is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of boron compounds which may be used as an activating cocatalyst for the present invention are tri-substituted ammonium salts such as:
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethyl-N-dodecylammonium tetrakis(pentafluorophenyl)borate,
N,N-dimethyl-N-octadecylammonium tetrakis(pentafluorophenyl)borate,
N-methyl-N,N-didodecylammonium tetrakis(pentafluorophenyl)borate,
N-methyl-N,N-dioctadecylammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6-tetrafluorophenyl)borate,
N,N-dimethylanilinium tetrakis(4-(triisopropylsilyl)-2, 3, 5, 6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
trimethylammonium tetrakis(2,3,4,6-tetrafluorophenyl)borate,
triethylammonium tetrakis(2,3,4,6-tetrafluorophenyl)borate,
tripropylammonium tetrakis(2,3,4,6-tetrafluorophenyl)borate,
tri(n-butyl)ammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl)borate, and
N,N-dimethyl-2,4,6-trimethylanilinium tetrakis(2,3,4,6-tetrafluorophenyl)borate;
disubstituted ammonium salts such as:
di-(i-propyl)ammonium tetrakis(pentafluorophenyl)borate, and
dicyclohexylammonium tetrakis(pentafluorophenyl)borate;
trisubstituted phosphonium salts such as:
triphenylphosphonium tetrakis(pentafluorophenyl)borate,
tri(o-tolyl)phosphonium tetrakis(pentafluorophenyl)borate, and
tri(2,6-dimethylphenyl)phosphonium tetrakis(pentafluorophenyl)borate;
disubstituted oxonium salts such as:
diphenyloxonium tetrakis(pentafluorophenyl)borate,
di(o-tolyl)oxonium tetrakis(pentafluorophenyl)borate, and
di(2,6-dimethylphenyl)oxonium tetrakis(pentafluorophenyl)borate;
disubstituted sulfonium salts such as:
diphenylsulfonium tetrakis(pentafluorophenyl)borate,
di(o-tolyl)sulfonium tetrakis(pentafluorophenyl)borate, and
bis(2,6-dimethylphenyl)sulfonium tetrakis(pentafluorophenyl)borate.

Preferred $(L^*-H)^+$ cations are N,N-dimethylanilinium, tributylammonium, N-methyl-N,N-didodecylammonium, N-methyl-N,N-dioctadecylammonium, and mixtures thereof.

Another suitable ion forming, activating cocatalyst comprises a salt of a cationic oxidizing agent and a noncoordinating, compatible anion represented by the formula:

$$(Ox^{e+})_d(A^{d-})_e.$$

wherein $Ox^{e+}$, $A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$$\copyright^+A^-$$

wherein:
$\copyright^+$ and $A^-$ are as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula:

$$R^=_3Si^+A^-$$

wherein:

$R^=$ is $C_{1-10}$ hydrocarbyl, and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is claimed in U.S. Ser. No. 08/304,314, filed Sep. 12, 1994 now U.S. Pat. No. 5,625,087.

Certain complexes of alcohols, mercaptans, silanols, and oximes with tris(pentafluorophenyl)borane are also effective catalyst activators and may be used for the present invention. Such cocatalysts are disclosed in U.S. Pat. No. 5,296,433, the teachings of which are herein incorporated by reference.

The most preferred activating cocatalysts are trispentafluorophenylborane and N,N-dioctadecyl-N-methylammonium tetrakispentafluorophenylborate. The latter compound being the principal component of a mixture of borate salts derived from bis(hydrogenated tallow)methylammonium compounds, which mixture may be used as the activating cocatalyst herein.

The molar ratio of metal complex: activating cocatalyst employed preferably ranges from 1:10 to 2:1, more preferably from 1:5 to 1.5:1, most preferably from 1:5 to 1:1.

Other activators include the previously described aluminoxanes. Preferred aluminoxanes include methylaluminoxane, propylaluminoxane, isobutylaluminoxane, combinations thereof and the like. So-called modified methylaluminoxane (MMAO) is also suitable for use as a cocatalyst. One technique for preparing such modified aluminoxane is disclosed in U.S. Pat. No. 4,960,878 (Crapo et al.), the disclosure of which is incorporated herein by reference. Aluminoxanes can also be made as disclosed in U.S. Pat. No. 4,544,762 (Kaminsky et al.); U.S. Pat. No. 5,015,749 (Schmidt et al.); U.S. Pat. No. 5,041,583 (Sangokoya): U.S. Pat. No. 5,041,584 (Crapo et al); and U.S. Pat. No. 5,041,585 (Deavenport et al.), the disclosures of all of which are incorporated herein by reference. When aluminoxanes are used as the activating cocatalyst, the molar ratio of transition metal complex: aluminum preferably ranges from 1:2,000 to 2:1, more preferably from 1:1,000 to 1.5:1, most preferably from 1:500 to 1:1.

In general, the polymerization may be accomplished at conditions well known in the prior art for Ziegler-Natta or Kaminsky-Sinn type polymerization reactions, that is, temperatures from 0-250° C., preferably 30 to 200° C. and pressures from atmospheric to 30,000 atmospheres or higher. Suspension, solution, slurry, gas phase, solid state powder polymerization or other process condition may be employed if desired. A solid component (other than that used to prepare the catalysts used to make the ethylene homopolymer of the present invention), may be employed especially silica, alumina, or a polymer (especially poly(tetrafluoroethylene) or a polyolefin), and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents for polymerization are inert liquids. Examples include straight and branched-chain hydrocarbons such as isobutane, butane, pentane, hexane, heptane, octane, and mixtures thereof, cyclic and alicyclic hydrocarbons such as cyclohexane, cycloheptane, methylcyclohexane, methylcycloheptane, and mixtures thereof, perfluorinated hydrocarbons such as perfluorinated $C_{4-10}$ alkanes, and the like and aromatic and alkyl-substituted aromatic compounds such as benzene, toluene, xylene, ethylbenzene and the like. Suitable solvents also include liquid olefins which may act as monomers or comonomers including ethylene, propylene, butadiene, cyclopentene, 1-hexene, 1-hexane, 4-vinylcyclohexene, vinylcyclohexane, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

b) Blend Compositions of the Ethylene Homopolymer with Heterogeneous Broad Composition Distribution Ethylene Interpolymers.

Blends of the ethylene homopolymers can also be prepared with heterogeneous broad composition distribution ethylene interpolymers. The heterogeneous component is differentiated from the homogeneous component in that in the latter, substantially all of the interpolymer molecules have the same ethylene/comonomer ratio within that interpolymer, whereas heterogeneous interpolymers are those in which the interpolymer molecules do not have the same ethylene/comonomer ratio. The term "broad composition distribution" used herein describes the comonomer distribution for heterogeneous interpolymers and means that the heterogeneous interpolymers have a "linear" fraction and that the heterogeneous interpolymers have multiple melting peaks (i.e., exhibit at least two distinct melting peaks) by DSC. The heterogeneous interpolymers and polymers have a degree of branching less than or equal to 2 methyls/1000 carbons in about 10 percent (by weight) or more, preferably more than about 15 percent (by weight), and especially more than about 20 percent (by weight). The heterogeneous interpolymers also have a degree of branching equal to or greater than 25 methyls/1000 carbons in about 25 percent or less (by weight), preferably less than about 15 percent (by weight), and especially less than about 10 percent (by weight).

The heterogeneous interpolymer component of the blend can also be an ethylene homopolymer or, preferably, interpolymers of ethylene with at least one comonomer selected from the group consisting of a compound represented by the formula $H_2C=CHR$ wherein R is a $C_1$-$C_{18}$ linear, branched or cyclic alkyl group or a $C_6$-$C_{20}$ aryl group, and a $C_4$-$C_{20}$ linear, branched or cyclic diene. Illustrative examples of the compounds represented by the formula $H_2C=CHR$ include propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, vinylcyclohexene and styrene. Illustrative examples of $C_4$-$C_{20}$ linear, branched and cyclic dienes include 1,3-butadiene, 1,4-pentadiene, 1,5-hexadiene, 1,4-hexadiene and cyclo hexadiene. Of these, propylene, 1-butene, 1-pentene, 1-hexene, 4-methyl-1-pentene, 1-octene, 1-decene, 1-dodecene, 1-tetradecene, 1-hexadecene, 1-octadecene and 1-eicosene are especially preferred. Heterogeneous interpolymers of ethylene and 1-butene, 1-pentene, 1-hexene and 1-octene are most preferred.

Ziegler-Natta catalysts may be used to prepare the heterogeneous component of the polymer blend. Preferred Ziegler-Natta catalysts include magnesium alkoxide-based catalysts, such as those taught by U.S. Pat. No. 4,526,943, U.S. Pat. Nos. 4,426,316, 4,661,465, U.S. Pat. No. 4,783,512, and U.S. Pat. No. 4,544,647, the disclosures of each of which are herein incorporated by reference. Such catalysts are particularly useful if the heterogeneous polymer component is to be prepared under slurry process conditions.

Additional examples of Ziegler-type catalysts which are particularly useful if the heterogeneous polymer blend component is to be prepared under the high polymerization temperatures of the solution process, include catalysts derived from organomagnesium compounds, alkyl halides or aluminum halides or hydrogen chloride, and a transition metal compound. Examples of such catalysts are described in U.S. Pat. No. 4,314,912 (Lowery, Jr. et al.), U.S. Pat. No. 4,547,475 (Glass et al.), and U.S. Pat. No. 4,612,300 (Coleman, III), the teachings of which are incorporated herein by reference.

Particularly suitable organomagnesium compounds include, for example, hydrocarbon soluble dihydrocarbylmagnesium such as the magnesium dialkyls and the magnesium diaryls. Exemplary suitable magnesium dialkyls include particularly n-butyl-sec-butylmagnesium, diisopropylmagnesium, di-n-hexylmagnesium, isopropyl-n-butylmagnesium, ethyl-n-hexylmagnesium, ethyl-n-butylmagnesium, di-n-octylmagnesium and others wherein the alkyl has from 1 to 20 carbon atoms. Exemplary suitable magnesium diaryls include diphenylmagnesium, dibenzylmagnesium and ditolylmagnesium. Suitable organomagnesium compounds include alkyl and aryl magnesium alkoxides and aryloxides and aryl and alkyl magnesium halides with the halogen-free organomagnesium compounds being more desirable.

Among the halide sources which can be employed herein are the active non-metallic halides, metallic halides, and hydrogen chloride. Suitable non-metallic halides are represented by the formula R'X wherein R' is hydrogen or an active monovalent organic radical and X is a halogen. Particularly suitable non-metallic halides include, for example, hydrogen halides and active organic halides such as t-alkyl halides, allyl halides, benzyl halides and other active hydrocarbyl halides wherein hydrocarbyl is as defined hereinbefore. By an active organic halide is meant a hydrocarbyl halide that contains a labile halogen at least as active, i.e., as easily lost to another compound, as the halogen of sec-butyl chloride, preferably as active as t-butyl chloride. In addition to the organic monohalides, it is understood that organic dihalides, trihalides and other polyhalides that are active as defined herein before are also suitably employed. Examples of preferred active non-metallic halides include hydrogen chloride, hydrogen bromide, t-butyl chloride, t-amyl bromide, allyl chloride, benzyl chloride, crotyl chloride, methylvinyl carbinyl chloride, α-phenylethyl bromide, diphenyl methyl chloride and the like. Most preferred are hydrogen chloride, t-butyl chloride, allyl chloride and benzyl chloride.

Suitable metallic halides which can be employed herein include those represented by the formula $MR_{y-a}X_a$ wherein:

M is a metal of Groups IIB, IIIA or IVA of Mendeleev's Periodic Table of Elements.

R is a monovalent organic radical,

X is a halogen,

Y has a value corresponding to the valence of M, and a has a value from 1 to y.

Preferred metallic halides are aluminum halides of the formula $AlR_{3-a}X_a$ wherein:

each R is independently hydrocarbyl as hereinbefore defined such as alkyl,

X is a halogen; and a is a number from 1 to 3.

Most preferred are alkylaluminum halides such as ethylaluminum sesquichloride, diethylaluminum chloride, ethylaluminum dichloride, and diethylaluminum bromide, with ethylaluminum dichloride being especially preferred. Alternatively, a metal halide such as aluminum trichloride or a combination of aluminum trichloride with an alkyl aluminum halide or a trialkyl aluminum compound may be suitably employed.

It is understood that the organic moieties of the aforementioned organomagnesium, e.g., R", and the organic moieties of the halide source, e.g., R and R', are suitably any other organic radical provided that they do not contain functional groups that poison conventional Ziegler catalysts.

The magnesium halide can be preformed from the organomagnesium compound and the halide source or it can be formed in situ in which instance the catalyst is preferably prepared by mixing in a suitable solvent or reaction medium (1) the organomagnesium component and (2) the halide source, followed by the other catalyst components.

Any of the conventional Ziegler-Natta transition metal compounds can be usefully employed as the transition metal component in preparing the supported catalyst component. Typically, the transition metal component is a compound of a Group IVB, VB, or VIB metal. The transition metal component is generally, represented by the formulas: $TrX'_{4-q}(OR^1)_q$, $TrX'_{4-q}R^2_q$, $VOX'_3$ and $VO(OR^1)_3$.

Tr is a Group IVB, VB, or VIB metal, preferably a Group IVB or VB metal, preferably titanium, vanadium or zirconium, q is 0 or a number equal to or less than 4, X' is a halogen, and $R^1$ is an alkyl group, aryl group or cycloalkyl group having from 1 to 20 carbon atoms, and $R^2$ is an alkyl group, aryl group, aralkyl group, substituted aralkyls, and the like. The aryl, aralkyls and substituted aralkyls contain 1 to 20 carbon atoms, preferably 1 to 10 carbon atoms. When the transition metal compound contains a hydrocarbyl group, $R^2$, being an alkyl, cycloalkyl, aryl, or aralkyl group, the hydrocarbyl group will preferably not contain an H atom in the position beta to the metal carbon bond. Illustrative but non-limiting examples of aralkyl groups are methyl, neo-pentyl, 2,2-dimethylbutyl, 2,2-dimethylhexyl; aryl groups such as benzyl; cycloalkyl groups such as 1-norbornyl. Mixtures of these transition metal compounds can be employed if desired.

Illustrative examples of the transition metal compounds include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_6H_{13})_2Cl_2$, $Ti(OC_8H_{17})_2Br_2$, and $Ti(OC_{12}H_{25})Cl_3$, $Ti(O-i-C_3H_7)_4$, and $Ti(O-n-C_4H_9)_4$.

Illustrative examples of vanadium compounds include $VCl_4$, $VOCl_3$, $VO(OC_2H_5)_3$, and $VO(OC_4H_9)_3$.

Illustrative examples of zirconium compounds include $ZrCl_4$, $ZrCl_3(OC_2H_5)$, $ZrCl_2(OC_2H_5)_2$, $ZrCl(OC_2H_5)_3$, $Zr(OC_2H_5)_4$, $ZrCl_3(OC_4H_9)$, $ZrCl_2(OC_4H_9)_2$, and $ZrCl(OC_4H_9)_3$.

As indicated above, mixtures of the transition metal compounds may be usefully employed, no restriction being imposed on the number of transition metal compounds which may be contracted with the support. Any halogenide and alkoxide transition metal compound or mixtures thereof can be usefully employed. The previously named transition metal compounds are especially preferred with vanadium tetrachloride, vanadium oxychloride, titanium tetraisopropoxide, titanium tetrabutoxide, and titanium tetrachloride being most preferred.

Suitable catalyst materials may also be derived from a inert oxide supports and transition metal compounds. Examples of such compositions suitable for use in the solution polymerization process are described in U.S. Pat. No. 5,420,090 (Spencer. et al.), the teachings of which are incorporated herein by reference.

The inorganic oxide support used in the preparation of the catalyst may be any particulate oxide or mixed oxide as previously described which has been thermally or chemically dehydrated such that it is substantially free of adsorbed moisture.

The specific particle size, surface area, pore volume, and number of surface hydroxyl groups characteristic of the inorganic oxide are not critical to its utility in the practice of the invention. However, since such characteristics determine the amount of inorganic oxide to be employed in preparing the catalyst compositions, as well as affecting the properties of polymers formed with the aid of the catalyst compositions, these characteristics must frequently be taken into consideration in choosing an inorganic oxide for use in a particular aspect of the invention. In general, optimum results are usually obtained by the use of inorganic oxides having an average particle size in the range of about 1 to 100 microns, preferably about 2 to 20 microns; a surface area of about 50 to 1,000 square meters per gram, preferably about 100 to 400 square meters per gram; and a pore volume of about 0.5 to 3.5 cm$^3$ per gram; preferably about 0.5 to 2 cm$^3$ per gram.

In order to further improve catalyst performance, surface modification of the support material may be desired. Surface modification is accomplished by specifically treating the support material such as silica, alumina or silica-alumina with an organometallic compound having hydrolytic character. More particularly, the surface modifying agents for the support materials comprise the organometallic compounds of the metals of Group IIA and IIIA of the Periodic Table. Most preferably the organometallic compounds are selected from magnesium and aluminum organometallics and especially from magnesium and aluminum alkyls or mixtures thereof represented by the formulas and $R^1MgR^2$ and $R^1R^2AlR^3$ wherein each of $R^1$, $R^2$ and $R^3$ which may be the same or different are alkyl groups, aryl groups, cycloalkyl groups, aralkyl groups, alkoxide groups, alkadienyl groups or alkenyl groups. The hydrocarbon groups $R^1$, $R^2$ and $R^3$ can contain between 1 and 20 carbon atoms and preferably from 1 to about 10 carbon atoms.

The surface modifying action is effected by adding the organometallic compound in a suitable solvent to a slurry of the support material. Contact of the organometallic compound in a suitable solvent and the support is maintained from about 30 to 180 minutes and preferably form 60 to 90 minutes at a temperature in the range of 20° to 100° C. The diluent employed in slurrying the support can be any of the solvents employed in solubilizing the organometallic compound and is preferably the same.

(c) Blend Compositions of the Ethylene Homopolymer with Polyolefin Compositions Having a Molecular Weight Maximum Occurring in the Fraction Having the Highest Comonomer Content.

Blends of the ethylene homopolymers can also be prepared with polyolefin compositions having a molecular weight maximum occurring in that part of the composition that has the highest comonomer content. A process for the preparation of these compositions under slurry process conditions is disclosed in Japanese Application Serial No. 148392/96 filed May 17, 1996, the entire contents of which are incorporated herein by reference. Said polymer compositions comprise a copolymer of ethylene with at least one comonomer selected from the group consisting of a compound represented by the formula $H_2C=CHR$ wherein R is a $C_1$-$C^{18}$ linear, branched or cyclic alkyl group or a $C_6$-$C_{20}$ aryl group, and a $C_4$-$C_{20}$ linear, branched or cyclic diene.

These polymer compositions also have the following properties (1) to (5):

(1) a density d (g/cm$^3$) of from 0.870 to 0.980;

(2) an Mw/Mn of from 2.5 to 10, preferably which satisfies the following inequalities;

$$1.25 \log M_w - 2.5 \leq M_w/M_n \leq 3.5 \log M_w - 11.0$$

wherein $M_w$ and $M_n$ are, respectively, a weight average molecular weight and a number average molecular weight, both as measured by gel permeation chromatography (GPC);

(3) within a range in molecular weight of the ethylene copolymer which is defined by the formula (IV):

$$\log(Mt) - \log(Mc) \leq 0.5 \qquad (IV)$$

wherein:

Mt is a point in molecular weight on a molecular weight distribution profile at which the profile shows a peak having a maximum intensity, and Mc is an arbitrary point in molecular weight on the molecular weight distribution profile, the molecular weight distribution profile being obtained together with a comonomer content distribution profile by subjecting the ethylene copolymer to gel permeation chromatography/Fourier transformation infrared spectroscopy (GPC/FT-IR); and an approximate straight line obtained from the comonomer content distribution profile by the least squares method has a gradient within the range defined by the formula (V):

$$0.0005 \leq \{C(Mc^1) - C(Mc^2)\}/(\log Mc^1 - \log Mc^2) \leq 0.05 \qquad (V)$$

wherein:

$Mc^1$ and $Mc^2$ are two different arbitrary points (Mc) in molecular weight which satisfy the formula (I), and $C(Mc^1)$ and $C(Mc^2)$ are, respectively, comonomer contents corresponding to $Mc^1$ and $Mc^2$ on the approximate straight line;

In the present invention, it is preferred that, within the above-defined range in molecular weight of the ethylene copolymer, the above-mentioned gradient be within the range defined by the formula (IV):

$$0.001 \leq \{C(Mc^1) - C(Mc^2)\}/(\log Mc^1 - \log Mc^2) \leq 0.02 \qquad (IV)$$

wherein $Mc^1$, $Mc^2$, $C(Mc^1)$ and $C(Mc^2)$ are as defined for the formula (V).

(4) when, in cross fractionation chromatography (CFC) of the ethylene copolymer, with respect to extraction at an arbitrary temperature T(° C.) falling within the range of between a first temperature at which a maximum amount of extraction is exhibited and a second temperature which is 10° C. higher than the first temperature, the relationship between the arbitrary temperature T(° C.) and a point in molecular weight on a molecular weight distribution profile of a copolymer fraction extracted at the arbitrary temperature T(° C.) at which point in molecular weight the molecular weight distribution profile of the copolymer fraction shows a peak having a maximum intensity is treated by the least squares method to obtain an approximate straight line, the approximate straight line has a gradient within the range defined by the formula (VI):

$$-1 \leq \{\log Mp(T^1) - \log Mp(T^2)\}/(T^1-T^2) \leq -0.005 \quad (VI)$$

wherein:

$T^1$ and $T^2$ are two different arbitrary extraction temperatures $T(°C.)$ within the range of between the first temperature and the second temperature, and $Mp(T^1)$ and $Mp(T^2)$ are, respectively, molecular weights corresponding to $T^1$ and $T^2$ on the approximate straight line; and Further, in the present invention, the gradient be preferably within the range defined by the formula:

$$-0.5 \leq \{\log Mp(T^1) - \log Mp(T^2)\}/(T^1-T^2) \leq -0.007;$$

preferably, $$-0.1 \leq \{\log Mp(T^1) - \log Mp(T^2)\}/(T^1-T^2) \leq -0.01;$$

more preferably, $$-0.08 \leq \{\log Mp(T^1) - \log Mp(T^2)\}/(T^1-T^2) \leq -0.02;$$

wherein $T^1$, $T^2$, $Mp(T^1)$ and $Mp(T^2)$ are as defined for the formula (VI).

(5) the measurement of the ethylene copolymer by CFC shows characteristics such that the sum of respective amounts of copolymer fractions extracted at temperatures which are at least 10° C. lower than the first temperature as defined above is 8% by weight or less, preferably 5% by weight or less, more preferably 3.5% by weight or less; based on the total amount of, excluding purge, copolymer fractions extracted at temperatures in the overall range of extraction temperatures in CFC.

The polyolefin compositions having a molecular weight maximum occurring in the fraction having the highest comonomer content are prepared by copolymerizing ethylene with a comonomer, under slurry polymerization conditions in the presence of the previously described constrained geometry catalysts and the solid component used to prepare the ethylene homopolymers of the present invention. The copolymerization reaction is conducted by slurry polymerization using the conditions previously defined for preparation of the ethylene homopolymers of the present invention.

As a diluent to be used for slurry polymerization, the inert solvents, which are mentioned above in connection with the preparation of the solid catalyst system, can be suitably used. Especially, isobutane, isopentane, heptane, hexane and octane are preferred.

It is also important that the copolymerization reaction is performed at a diffusion-limited rate. This means that the ethylene copolymer produced must maintain a powdery state during the polymerization reaction. Therefore, the upper limit of the polymerization temperature is extremely important and must remain below the melting point of the copolymer.

Also ethylene is copolymerized with at least one comonomer selected from the group consisting of a compound represented by the formula $H_2C=CHR$ wherein R is a $C_1$-$C_{18}$ linear, branched or cyclic alkyl group or a $C_6$-$C_{20}$ aryl group, and a $C_4$-$C_{20}$ linear, branched or cyclic diene. Illustrative examples of the compounds represented by the formula $H_2C=CHR$ include propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, vinylcyclohexene and styrene. Illustrative examples of $C_4$-$C_{20}$ linear, branched and cyclic dienes include 1,3-butadiene, 1,4-pentadiene, 1,5-hexadiene, 1,4-hexadiene and cyclohexadiene. Of these, propylene, 1-butene, 1-pentene, 1-hexene, 4-methyl-1-pentene, 1-octene, 1-decene, 1-dodecene, 1-tetradecene, 1-hexadecene, 1-octadecene and 1-eicosene are especially preferred.

The molecular weight of the ethylene copolymer produced can be controlled by changing the content of hydrogen in the reaction system or by changing the polymerization temperature, as described in DE 3127133.2.

(c) Blend Compositions of the Ethylene Homopolymer with a Second Ethylene Homopolymer.

Blends of the ethylene homopolymer of the present invention with a second ethylene homopolymer are also an aspect of the present invention. The second ethylene homopolymer can be one produced by a Ziegler catalyst, a Phillips type Cr—$SiO_2$ catalyst, or a metallocene-based single site catalyst including the constrained geometry catalysts, used to make the homogeneous narrow composition distribution ethylene interpolymer blend component. Also included as a the second homopolymer is a homopolymer of the present invention, having different properties from the first, which properties include for example, $I_2$, or $I_{21}/I_2$, or $I_{10}/I_2$, or density, or $M_w$, or $M_w/M_n$.

Preparation of the Blend Compositions.

If blends of the higher density ethylene homopolymer with further ethylene interpolymers or homopolymers as described herein, are required, each component can be made separately in different reactors, and subsequently blended together.

The blend compositions may also be produced via a continuous (as opposed to a batch or semi-batch operation) controlled polymerization process using at least one reactor. Preferably, though, the higher density ethylene interpolymer and the additional ethylene interpolymers of the blend compositions are made in a multiple reactor scheme, operated either in parallel or in series, such as those disclosed in U.S. Pat. No. 3,914,342 (Mitchell) and WO 94/00500, the teachings of which are hereby incorporated herein by reference. For example, at least two reactors operated in series, i.e., one after the other, may be used. Alternatively, the reactors may be operated in parallel, i.e., conducting the polymerization steps A and B in separate reactors and subsequently combining melt streams to yield a composite product blend. In the multiple reactor scheme, at least one of the reactors makes the higher density ethylene interpolymer using the supported metallocene catalyst described herein, under gas phase or slurry process conditions, and at least one of the reactors makes the additional components of the blend using the required single or multiple catalysts at polymerization temperatures, pressures and feed concentrations required to produce the polymer with the desired properties. The reactors may be any of the type commonly used for ethylene polymerization, including but not restricted to autoclave or loop-type reactors.

Thus in one embodiment, the ethylene homopolymer using the supported metallocene catalyst described herein, is made under slurry process conditions in a first reactor in Step A and the contents of the first reactor passed to a second reactor in which the feed concentrations and the temperature are adjusted, to form under slurry process conditions in Step B either a second ethylene homopolymer or, if comonomer is added, to form, the polyolefin component of the polymer blend having a molecular weight maximum occurring in the fraction having the highest comonomer content.

In a further embodiment, the higher density ethylene homopolymer using the supported metallocene catalyst described herein, is made under slurry process conditions in a first reactor in Step A and the contents of the first reactor passed to a second reactor in which the feed concentrations and the temperature are adjusted, and one or more of the Ziegler catalysts described herein added, to form, in Step B, under slurry process conditions, the heterogeneous ethylene interpolymer component of the polymer blend with the desired properties.

In a further embodiment the higher density ethylene homopolymer using the supported metallocene catalyst described herein, is made under slurry process conditions in a first reactor in Step A and the contents of the first reactor enter a second reactor in which the feed concentrations and temperatures are adjusted and one of the metallocene catalysts described herein is added to form the homogeneous component of the polymer blend with the desired properties in Step B under solution process conditions.

In a further embodiment, the higher density ethylene homopolymer using the supported metallocene catalyst described herein, is made under slurry process conditions in a first reactor in Step A and the contents of the first reactor passed to a second reactor in which the temperature and feed concentrations are adjusted, and one or more of the Ziegler catalysts described herein added, to form, in Step B, under solution process conditions, the heterogeneous ethylene interpolymer component of the polymer blend with the desired properties.

Additives such as antioxidants (e.g., hindered phenolics (e.g., Irganox™ 1010), phosphites (e.g., Irgafos™168)), cling additives (e.g., PIB), antiblock additives, pigments, fillers, and the like can also be included in the formulations, to the extent that they do not interfere with the enhanced formulation properties discovered by Applicants. Both Irganox™ and Irgafos™ are made by and trademarks of Ciba Geigy Corporation. Irgafos™ 168 is a phosphite stabilizer and Irganox™ 1010 is a hindered polyphenol stabilizer (e.g., tetrakis [methylene 3-(3,5-ditert.butyl-4-hydroxyphenylpropionate)] methane.

Properties of Blend Compositions Comprising the Higher Density Ethylene Homopolymer.

a) Properties of the Ethylene Homopolymer Blend Component.

The amount of the ethylene homopolymer of the present invention, incorporated into the blended compositions of the present invention is of from about 1 to about 99, preferably of from about 10 to about 90, more preferably of from about 25 to about 75, most preferably of from about 35 to about 65 percent, by weight based on the combined weights of Components A and B.

The properties of the ethylene homopolymer of the present invention, incorporated into the blended compositions of the present invention are as described previously.

b) Properties of the Homogeneous Narrow Composition Distribution Ethylene/α-Olefin Interpolymer Blend Component.

The amount of the homogeneous narrow composition distribution ethylene/α-olefin interpolymer incorporated into the blended compositions of the present invention is of from about 1 to about 99, preferably of from about 10 to about 90, more preferably of from about 25 to about 75, most preferably of from about 35 to about 65 percent, by weight based on the combined weights of components A and B.

The density of the homogeneous narrow composition distribution ethylene/α-olefin interpolymer incorporated into the blended composition of the present invention is generally of from about 0.870 to about 0.980, preferably of from about 0.890 to about 0.965, more preferably of from about 0.915 to about 0.955 g/cm³.

The melt index ($I_2$) for the homogeneous narrow composition distribution ethylene/α-olefin interpolymer incorporated into the blended composition of the present invention is generally of from about 0.0001 to about 10000, preferably of from about 0.001 to about 5000, more preferably of from about 0.01 to about 3000 g/10 min.

The $I_{21}/I_2$ ratio of the homogeneous narrow composition distribution ethylene/α-olefin interpolymer incorporated into the blended composition of the present invention is of from about 10 to about 50, preferably of from about 12 to about 45, more preferably of from about 15 to about 40 or the $I_{10}/I_2$ ratio of the homogeneous narrow composition distribution ethylene/α-olefin interpolymer incorporated into the blended composition of the present invention is of from about 5 to about 25, preferably of from about 5.3 to about 25, more preferably of from about 5.5 to about 20.

The $M_w/M_n$ ratio of the homogeneous narrow composition distribution ethylene/α-olefin interpolymer incorporated into the blended composition of the present invention (including the substantially linear ethylene/α-olefin interpolymer) is less than about 3.

c) Properties of the Heterogeneous Broad Composition Distribution Ethylene/α-Olefin Interpolymer Blend Component.

The amount of the heterogeneous broad composition distribution ethylene/α-olefin interpolymer incorporated into the blended compositions of the present invention is of from about 1 to about 99, preferably of from about 10 to about 90, more preferably of from about 25 to about 75, most preferably of from about 35 to about 65 percent, by weight based on the combined weights of components A and B.

The density of the heterogeneous broad composition distribution ethylene/α-olefin interpolymer incorporated into the blended composition of the present invention is generally of from about 0.870 to about 0.980, preferably of from about 0.890 to about 0.965, more preferably of from about 0.915 to about 0.955 g/cm³.

The melt index ($I_2$) for the heterogeneous broad composition distribution ethylene/α-olefin interpolymer incorporated into the blended composition of the present invention is generally of from about 0.0001 to about 10000, preferably of from about 0.001 to about 5000, more preferably of from about 0.01 to about 3000 g/10 min.

The $I_{21}/I_2$ ratio of the heterogeneous broad composition distribution ethylene/α-olefin interpolymer incorporated into the blended composition of the present invention is of from about 15 to about 80, preferably of from about 20 to about 70, more preferably of from about 25 to about 60 or the $I_{10}/I_2$ ratio of the heterogeneous broad composition distribution ethylene/α-olefin interpolymer incorporated into the blended composition of the present invention is of from about 5 to about 40, preferably of from about 5.3 to about 35, more preferably of from about 5.5 to about 30.

The $M_w/M_n$ ratio of the heterogeneous broad composition distribution ethylene/α-olefin interpolymer incorporated into the blended composition of the present invention is generally of from about 3 to about 12 preferably of from about 3.5 to about 10, more preferably of from about 4 to about 9.

d) Properties of the Polyolefin Composition Having a Molecular Weight Maximum Occurring in the Fraction Having the Highest Comonomer Content Blend Component.

The amount of polyolefin compositions having a molecular weight maximum occurring in the fraction having the highest comonomer content, incorporated into the blended compositions of the present invention is of from about 1 to about 99, preferably of from about 10 to about 90, more preferably of from about 25 to about 75, most preferably of from about 35 to about 65 percent, by weight based on the combined weights of Components A and B.

The density of the polyolefin compositions having a molecular weight maximum occurring in the fraction having the highest comonomer content incorporated into the blended compositions of the present invention is generally of from about 0.870 to about 0.980, preferably of from about 0.890 to about 0.965, more preferably of from about 0.915 to about 0.955 g/cm$^3$.

The melt index of the polyolefin compositions having a molecular weight maximum occurring in the fraction having the highest comonomer content incorporated into the blended compositions of the present invention is generally of from about 0.0001 to about 10000, preferably of from about 0.001 to about 5000, more preferably of from about 0.01 to about 3000 g/10 min.

The $I_{21}/I_2$ ratio of the polyolefin compositions having a molecular weight maximum occurring in the fraction having the highest comonomer content, incorporated into the blended compositions of the present invention is of from about 15 to about 65, preferably of from about 18 to about 55, more preferably of from about 20 to about 50 or the $I_{10}/I_2$ ratio of the polyolefin compositions having a molecular weight maximum occurring in the fraction having the highest comonomer content, incorporated into the blended compositions of the present invention is of from about 5 to about 30, preferably of from about 5 to about 28, more preferably of from about 5.5 to about 25.

The $M_w/M_n$ ratio of the polyolefin compositions having a molecular weight maximum occurring in the fraction having the highest comonomer content, incorporated into the blended compositions of the present invention is generally of from about 2.5 to about 10 preferably of from about 2.8 to about 8, more preferably of from about 3 to about 7.

d) Properties of the Second Homopolymer Blend Component.

The amount of the second homopolymer, incorporated into the blended compositions of the present invention is of from about 1 to about 99, preferably of from about 10 to about 90, more preferably of from about 25 to about 75, most preferably of from about 35 to about 65 percent, by weight based on the combined weights of Components A and B.

The density of the second homopolymer incorporated into the blended compositions of the present invention is generally of from about 0.870 to about 0.980, preferably of from about 0.890 to about 0.965, more preferably of from about 0.915 to about 0.955 g/cm$^3$.

The melt index of the second homopolymer incorporated into the blended compositions of the present invention is generally of from about 0.0001 to about 10000, preferably of from about 0.001 to about 5000, more preferably of from about 0.01 to about 3000 g/10 min.

The $I_{21}/I_2$ ratio of the second homopolymer, incorporated into the blended compositions of the present invention is of from about 18 to about 70, preferably of from about 20 to about 60, more preferably of from about 10 to about 50 or the $I_{10}/I_2$ ratio of the second homopolymer, incorporated into the blended compositions of the present invention is of from about 5 to about 40, preferably of from about 5.3 to about 35, more preferably of from about 5.5 to about 30.

The $M_w/M_n$ ratio of the second homopolymer, incorporated into the blended compositions of the present invention is generally of from about 2.5 to about 12, preferably of from about 2.8 to about 10, more preferably of from about 3 to about 9.

f) Properties of the Final Blend Compositions

The density of the final blend compositions of the present invention is generally from about generally of from about 0.870 to about 0.980. preferably of from about 0.915 to about 0.975, more preferably of from about 0.935 to about 0.970 g/cm$^3$.

The melt index of the final blend compositions of the present invention is generally of from about 0.0001 to about 10000 preferably of from about 0.001 to about 5000, more preferably of from about 0.01 to about 3000 g/10 min The $I_{21}/I_2$ ratio of the final blend compositions of the present invention is of from about 20 to about 200, preferably of from about 30 to about 180, more preferably of from about 40 to about 150 or the $I_{10}/I_2$ ratio of the final blend compositions of the present invention is of from about 5 to about 100, preferably of from about 5 to about 90, more preferably of from about 5 to about 80.

The $M_w/W_n$ ratio of the final blend compositions of the present invention is generally of from about 2.5 to about 50, preferably of from about 3 to about 45, more preferably of from about 5 to about 40.

Possible applications for the novel resin blends taught by the present invention include pipe, especially pipe used in high temperature applications, geomembranes, wire and cable jacketing, thermoformed articles, stackable plastic pallets, blow molded bottles and containers, rotomolded articles, films, including thick film applications such as environmental pond liners, and vinyl benzocyclobutene cross linking.

The present invention is now illustrated by, but is by no means limited to, the following examples.

EXAMPLES

Test Methods

Tensile Properties

The tensile properties of the molded materials were measured in accordance with ASTM D 638-76. Tensile strength, yield, toughness and 2% secant modulus of the films was measured in accordance with ASTM D-882; PPT tear was measured in accordance with ASTM D-2582.

Modulus Of Elasticity

The modulus of elasticity of the materials was measured in accordance with ISO 527.

Viscosity Number

The viscosity number of the materials in decaline was measured in accordance with ISO 1191.

Haze.

Haze was measured on a 0.5 mm thick compression molded specimen according to ASTM D 1003.

Impact Strength

The Double-V notched impact strength of the materials was measured in accordance with DIN 53753 (1J pendulum).

Ball Indentation Hardness

The ball indentation hardness of the materials was measured in accordance with ISO 527.

Impact Properties

The impact properties were evaluated in accordance with JIS-K7111.

Critical Strain Energy Release Rate

The critical strain energy release rate $G_C$ was measured in the Charpy mode, in accordance with the procedure described by E. Plati and J. G. Williams in Polymer Engineering and Science, June, 1975, Volume 15, No 6, pp. 470 to 477. For each temperature at least 6 samples are used. The sample dimensions are 125 mm×10 mm×10 mm. The bars are machined out of thick compression molded sheets. The procedure used to mold these sheets was a modification of the procedure outlined in "A compression molding technique for thick sheets of thermoplastics" by M. J. Cawood and G. A. H. Smith in Polymer Testing 1 (1980), 3-7, was used:

Thus the polymer granules or powders were compression molded in a 10 mm thick mold, laterally insulated using Teflon™. They were heated up to 160° C. and kept at 6.7 MPa for three minutes followed by three one minute cycles of exertion and release. Excessive flash was removed. The material was then heated to 180° C. and kept for about 5 minutes at 6.7 MPa, which was also exerted and released for 3 cycles of one minute each. Finally the melt was solidified under a pressure of 1.7 MPa and slowly cooled overnight by switching of the heating.

Bending ESCR Test

The Bending ESCR Test was carried out in 10 wt % of surface-active agent solution in accordance with JIS-K6760. The testing temperature was 50° C. or 80° C.

Pennsylvania Notch Test (PENT)

The Pennsylvania Notch Test is a slow crack growth test, performed following the procedure described by X. Lu and N. Brown, Polymer Testing 11 (1992), pages 309319. The test is conducted at 2.4 MPa and 80° C. The sample dimensions are 50 mm×25 mm×10 mm and are machined from the same sheet as the $G_C$ bars.

Rheological Parameters

Viscosities were measured on an Rheometrics mechanical spectrometer at 190° C. in the oscillatory mode.

Infrared Analysis

Comonomer content was measured using infrared spectroscopy on a Beckman IR2450 Spectrophotometer.

Intrinsic Tear

Intrinsic tear was measured on the compression molded sheet using the Elmendorf tear (type B) method as described in ASTM D-1922.

Determination of the Slope of Strain Hardening Coefficient

The slope of strain hardening is measured by compression molding a plaque from the polymer to be tested. Typically, the plaque is molded at about 177° C. for 4 minutes under almost no pressure and then pressed for 3 minutes under a pressure of about 200 psi. The plaque is then allowed to cool at about 8° C./minute while still under 200 psi pressure. The molded plaque has a thickness of about 0.005 inches. The plaque is then cut into a dogbone shaped test piece using a steel rule die. The test piece is 0.315 inches wide and 1.063 inches long. The start of the curved portion of the dogbone shape begins at 0.315 inches from each end of the sample and gently curves (i.e., tapers) to a width of 0.09 inches. The curve ends at a point 0.118 inches from the start of the curve such that the interior portion of the dogbone test piece has a width of 0.09 inches and a length of 0.197 inches.

The tensile properties of the test sample is tested on an Instron Tensile Tester at a crosshead speed of 1 inch/minute. The slope of strain hardening is calculated from the resulting tensile curve by drawing a line parallel to the strain hardening region of the resulting stress/strain curve. The strain hardening region occurs after the sample has pulled its initial load ((i.e., stress) usually with little or no elongation during the initial load) and after the sample has gone through a slight drawing stage (usually with little or no increase in load, but with increasing elongation (i.e., strain)). In the strain hardening region, the load and the elongation of the sample both continue to increase. The load increases in the strain hardening region at a much lower rate than during the initial load region and the elongation also increase, again at a rate lower than that experienced in the drawing region. The slope of the parallel line in the strain hardening region is then determined.

The slope of strain hardening coefficient (SHC) is calculated according to the following equation:

$$SHC = (\text{slope of strain hardening}) * (I_2)^{0.25}$$

where $I_2$=melt index in grams/10 minutes.

a) The Ethylene Homopolymer.

The following examples illustrate the unique molecular density vs $I_2$ and $M_w$ vs $M_w/M_n$ relationships of the ethylene homopolymers of the current invention as compared to;

a) ethylene homopolymer products of Ziegler catalysts made under slurry phase process conditions (Comparative Experiments A-F), b) ethylene homopolymer products of unsupported, constrained geometry catalyst made under solution process conditions, (Comparative Experiments G-AB), c) ethylene homopolymer products of supported, single site catalyst made under slurry process conditions (Comparative Experiments AC-AK), and d) an ethylene homopolymer product of a supported, single site catalyst made under gas phase process conditions (Comparative Experiment AL).

Example 1

Catalyst Preparation.

The supported cocatalyst was a silica/methylalumoxane support having the properties of and prepared substantially as described in WO 96/16092 (prepared by Witco GmbH, lot No. TA 02794/HL/30) containing between 23 and 25 weight percent of aluminum. A 100 g sample of the support was slurried for four hours in 800 ml of hexane to which was added an Isopar™ E (Exxon) solution of the constrained geometry catalyst {(tert-butylamido)dimethyl(tetramethyl-$\eta^5$-cyclopentadienyl)silane}dimethyl-titanium(IV) sufficient to obtain a final catalyst loading of 40 micromole of titanium for one gram of support. The catalyst was transferred to the catalyst feed vessel of the plant. In this vessel, the supported catalyst was further diluted with isopentane to obtain a concentration of 0.5 micromole titanium per ml. This catalyst is abbreviated as "CGC/MAO" in Table 1.

Polymerization

The polymerization was performed in a continuous slurry process using a single reactor mode. The reactor volume was 10 liter, and was operated at a constant level of about 65%, and agitated at 800 rpm using a Lightnin A310 mixing blade. The reactor temperature was kept constant by jacket cooling and the melt index of the produced polymer controlled via hydrogen addition. All feed streams were introduced to the reactor through dip pipe legs in the liquid phase to allow intimate mixing. The ethylene flow was kept constant during the polymerization and the reactor pressure controlled by the amount of catalyst fed to the reactor. Based on the ethylene flow, the isopentane diluent flow was adapted to obtain a certain percentage of solids in the reactor. The reactor temperature for Example 1 was 80° C., the reactor pressure was 14.6 bar, the ethylene feed rate was 1498 g/hr, the hydrogen feed rate was 0.271 Nl/hr, no comonomer was used. The isopentane feed rate was 3500 g/hr.

Examples 2-7

Examples 2-7 were produced in a similar fashion to Example 1, but using the process conditions listed in Table 2.

Examples 8-14

Catalyst Preparation.

The catalyst used was the combination of a silica-supported borate activator and a constrained geometry prepared essentially as described in WO 96/28480, Example 28. This catalyst was given the abbreviation of "CGC/Borate" in Table 1.

Polymerization.

Examples 8-14 were produced in a similar fashion as Example 1, but using the process conditions listed in Table 2.

Comparative Experiments A-C

Catalyst Preparation.

The comparative experiments A-C were produced, using the Ziegler-Natta supported catalyst as described in U.S. Pat. No. 4,661,465 (abbreviated as "Ziegler" in Table 3).

Polymerization.

The polymerization was performed in a continuous slurry process using a single reactor mode similar to that described for Example 1.

Comparative Experiments D-F

The comparative experiments D-F were produced as for Comparative Experiments A-C but in a commercial size slurry production facility, the process conditions of which are listed in Table 4.

Comparative Experiments G-AB

Catalyst Preparation.

The catalyst/cocatalyst system used was a mixture in Isopar™ E (Exxon) of solutions of the constrained geometry catalyst, {(tert-butylamido)dimethyl(tetramethyl-$\eta^5$-cyclopentadienyl)-silane}dimethyltitanium(IV) with the activator, tris(pentafluorophenyl) borane and isobutyl-modified methylalumoxane Akzo Chemical) in the respective molar ratios of 1:3:10. This catalyst was given the abbreviation of "CGC" in Table 3.

Polymerization

Comparative experiments G-AB were produced under solution process conditions. A continuous stirred tank reactor with a volume of five liters was used. Hydrogen, if added for control of melt index, was combined into one stream with the ethylene before being introduced into the diluent mixture. Typically, this diluent mixture comprises a mixture of C8-C10 saturated hydrocarbons (e.g. Isopar™ E, trademark of Exxon). The reactor feed mixture was continuously introduced into the reactor. The transition metal complex and the cocatalyst, dissolved in the same solvent, were combined into a single stream and were also continuously injected into the reactor. The reactor pressure was held at about 30 bar. Temperature was controlled by the catalyst flow and the use of a cooling jacket. In the outlet stream of the reactor antioxidants (1000 ppm Irganox™ B-900 (trademark of Ciba-Geigy)) were incorporated. This stream was taken to a heat exchanger where its temperature was raised to 270° C. and then to a devolatilizing unit where the solvent was separated from the polymer. The molten polymer was then carried to a pelletizer. The reactor conditions used for comparative experiments G-AB are listed in Table 4.

Comparative Experiments AC-AH

Catalyst Preparation a) Preparation of Phenylsilane-Modified Silica Support.

A heptane (350 ml) slurry of GRACE Davison 948 (800° C.; 0.5 mmol —OH/g) silica (30.0 g) was treated with PhMeH$_2$Si (9.15 g; 97 percent; 72.8 mmol) and NEt$_3$ (10.5 ml; 75 mmol). The resulting mixture was refluxed for 12 hours in an overhead stirrer under argon atmosphere. The resulting solution was cooled to 25 C and the phenylmethylsilane-modified silica product was collected on a frit under argon, washed with pentane (5×30 ml), and dried under reduced pressure. Yield: 31.73 g. DRIFTS IR: ν (Si—H) 2160 cm$^{-1}$ (s). $^{29}$Si CPMAS: δ-6 ppm.

b) Preparation of the Activator (dimethylanilinium (4-(4'-hydroxyphenyl)phenyl)tris-(pentafluorophenyl)borate borate, [PhMe$_2$NH]$^+$[(C$_6$F$_5$)$_3$B(C$_6$H$_4$—C$_6$H$_4$-p-OH.

i). Synthesis of 4-((4'-bromophenyl)phenoxy)trimethylsilane BrC$_6$H$_4$—C$_6$H$_4$-p-OSiMe$_3$ 1,1,1,3,3,3-Hexamethyldisilazane (75 ml; 98 percent purity; 0.348 mol) was added to BrC$_6$H$_4$—C$_6$H$_4$-p-OH (30 g; 0.117 mol) and heated to reflux for 4 hours. After cooling to 25° C., the solid product was filtered and rinsed with cold pentane (50 ml; 0° C.). The crude product was then dissolved in diethylether and purified by flash chromatography of silica (Davison 948, 800° C., pentane). The product was a white crystalline solid. Yield: 33.6 g (89 percent)

ii) Synthesis of MgBrC$_6$H$_4$—C$_6$H$_4$-p-OSiMe$_3$

Magnesium powder (50 mesh; 0.47 g; 19.3 mmol) was mixed with THF (5 ml) in a 3-necked flask. 1,2-dibromoethane (0.25 ml; 2.87 mmol) was then syringed into the flask and heated to reflux vigorously. A THF solution (11 ml) of BrC$_6$H$_4$—C$_6$H$_4$-p-OSiMe$_3$ (3.0 g; 9.34 mmol) was added dropwise through a syringe over a period of 20 minutes under reflux conditions. The resulting hot reaction mixture was cooled to 25° C. in 1.5 hours. The dark gray solution was filtered and titrated with 2-butanol in the presence of 5-methyl-1,10-phenanthroline. Yield: 87 percent (0.76 M, 10.9 ml).

iii). Synthesis of [MgBr.2THF][(C$_6$F$_5$)$_3$B(C$_6$H$_4$—C$_6$H$_4$-p-OSiMe$_3$)]

A solution of B(C$_6$F$_5$)$_3$ (3.24 g; 6.33 mmol) in 50 ml diethyl ether was treated with freshly prepared MgBrC$_6$H$_4$—C$_6$H$_4$-p-OSiMe$_3$ (10.4 ml; 0.76 M; 8.13 mmol) at room temperature. The reaction mixture was stirred for 16 hours, 100 ml pentane was added and the mixture further stirred for 30 minutes to form a two layer mixture. The upper pentane layer was decanted and the lower layer was further washed with pentane (50 ml) two times. The resulting syrup was evaporated under reduced pressure to obtain the white solid product. Yield: 6.84 g (84 percent)

iv) Synthesis of dimethylanilinium 4-((4'-hydroxyphenyl)phenyl)-tris(pentafluorophenyl)borate [PhMe$_2$NH]$^+$[(C$_6$F$_5$)$_3$B(C$_6$H$_4$—C$_6$H$_4$-p-OH)]$^-$

[MgBr.2THF][(C$_6$F$_5$)$_3$B(C$_6$H$_4$—C$_6$H$_4$-p-OSiMe$_3$)], (23:9 mmol) and aqueous NMe$_2$Ph.HCl solution (100 ml; 0.312 M; 31.2 mmol) were stirred at room temperature for 16 hours. The resulting H$_2$O solution was carefully decanted and the viscous solid was washed with distilled $H_2O$ (6×150 ml) and rinsed with pentane (3×100 ml) and dried under reduced pressure. Yield: 84 percent.

c) Preparation of Silica-Supported Activator (dimethylanilinium (4-(4'-hydroxyphenyl)phenyl)tris-(pentafluorophenyl)borate borate, [PhMe$_2$NH]$^+$ [(C$_6$F$_5$)$_3$B(C$_6$H$_4$—C$_6$H$_4$-p-O—SiHPh-Osilica)]-)

An ether (80 ml) slurry of the phenylsilane-modified silica (4.00 g) was treated with dimethylanilinium (4-(4'-hydroxyphenyl)-phenyl)tris(pentafluorophenyl)borate [PhMe$_2$NH]$^+$[(C$_6$F$_5$)$_3$B(C$_6$H$_4$-p-OH)]$^-$ (prepared according to 1A2(a-d) (1.20 g; 1.49 mmol) at 25 C under an argon atmosphere. The solution was agitated in dry box for 2 days and the resulting white solid was filtered off, washed with ether (5×20 ml) and pentane (3×20 ml), and dried under reduced pressure. Yield: 5.04 g. DRIFTS IR: v (Si—H) 2191 cm$^{-1}$ (m); v (N—H) 3244 cm$^{-1}$ (w). $^{29}$Si CPMAS: —O—SiHPh-OSilica (s, –41 ppm). $^{13}$C CPMAS: NHMe$_2$Ph (s, 47.7 ppm). ICP boron content: 0.225 percent d) Final Catalyst Preparation The final catalyst mixture was prepared by combining 81 mg (200 µmol) of (n-BuCp)$_2$ZrCl$_2$, 4.90 g of phenylsilane modified silica supported dimethylanilinium 4-(4'-hydroxyphenyl)phenyl)tris-(pentafluorophenyl)borate and 2 mmol triisobutylaluminum (TIBA) in 800 mL of hexane in the dry box and placing the mixture in a 1 L bomb. The contents were then transferred under nitrogen to the stirred catalyst vessel and diluted to 8 L with isopentane. This catalyst is given the abbreviation "bis Cp/Borate" in Table 3.

Polymerization

Examples AC-AH were produced in a similar fashion as Example 1, but using the process conditions listed in Table 4.

Comparative Experiments AI

Catalyst Preparation

As for Example AC except that the transition metal complex used was Me$_2$Si(IND)$_2$ZrCl$_2$ and the resulting catalyst was given the abbreviation "IND/Borate" in Table 3.

Polymerization

Examples AI was produced in a similar fashion as Example 1, but using the process conditions listed in Table 4.

Comparative Experiment AJ and AK.

The catalyst and polymerization procedure used was as prepared for Comparative Experiment AC and the homopolymer prepared using the process conditions listed in Table 4.

Comparative Experiment AL.

The comparative experiment AL was produced as for Example 1, but using the supported single site catalyst as described by Stehling et al. in U.S. Pat. No. 5,382,631.

TABLE 1*

| Examples | Catalyst type | I2.16 g/10 m | I21.6 g/10 m | I10/I2 — | Density g/cc | Mn g/mole | Mw g/mole | Mw/Mn — |
|---|---|---|---|---|---|---|---|---|
| 1** | CGC/MAO | 0.000378 | 0.02 | * | 0.9400 | | | |
| 2** | CGC/MAO | 0.010851 | 0.35 | | 0.9484 | | | |
| 3 | CGC/MAO | 8.65 | | 6.65 | 0.9778 | 20000 | 64500 | 3.23 |
| 4 | CGC/MAO | 26.4 | | 6.57 | 0.9737 | 16000 | 48600 | 3.04 |
| 5 | CGC/MAO | 0.31 | | 7.71 | | 47400 | 143000 | 3.02 |
| 6 | CGC/MAO | 0.21 | | 7.67 | | 49900 | 160000 | 3.21 |
| 7 | CGC/MAO | 0.15 | | 7.40 | | 56600 | 202000 | 3.57 |
| 8 | CGC/Borate | 5.68 | | 5.95 | 0.9674 | | | |
| 9 | CGC/Borate | 1.36 | | 8.19 | 0.9648 | | | |
| 10 | CGC/Borate | 0.12 | | | 0.9554 | 51200 | 295900 | 5.78 |
| 11 | CGC/Borate | 23.1 | | 5.8 | 0.9689 | 16700 | 51300 | 3.07 |
| 12 | CGC/Borate | | 1.75 | | | | | |
| 13 | CGC/Borate | | 1.35 | | | 36300 | 134300 | 3.70 |
| 14 | CGC/Borate | | <0.01 | | | 318300 | 844600 | 2.65 |

*Empty cell means data are not available
**I2 is calculated from I21 using: I21.6/I2.16 = (21.6/2.16)^(1/n) where log n = –0.1574 + 0.04645.log (I21.6) From: Shenoy, A. V., Chattopadhyay, S., Nadkarni, V. M., Rheologica Acta, 1983, 22, 90

TABLE 2*

| | Slurry Process | | | | | |
|---|---|---|---|---|---|---|
| Examples | Reactor temperature ° C. | Reactor pressure bar | Ethylene flow g/hr | Hydrogen flow Nl/hr | Isopentane flow g/hr | Reactor level % |
| 1 | 80 | 14.6 | 1498 | 0.271 | 3500 | 65 |
| 2 | 80 | 15.3 | 2500 | 0.495 | 4170 | 65 |
| 3 | 80 | 15 | 1200 | 0.21 | 3300 | 65 |
| 4 | 80 | 14 | 1600 | 0.488 | 3000 | 65 |
| 5 | 80 | 15 | 1600 | 1.1 | 5000 | 65 |
| 6 | 80 | 15 | 166 | 1.0 | 5000 | 65 |
| 7 | 80 | 15 | 1200 | 0.50 | 3300 | 65 |
| 8 | 80 | 15 | 1000 | 2.2 | 2500 | 70 |
| 9 | 80 | 5.2 | 650 | 0.7 | 2000 | 65 |
| 10 | 70 | 15 | 800 | 0.4 | 2500 | 65 |
| 11 | 70 | 15 | 750 | 2 | 2500 | 41 |
| 12 | 80 | 15 | 900 | 0.3 | 2500 | 65 |
| 13 | 70 | 15 | 1200 | 0.4 | 2500 | 66 |
| 14 | 60 | 9 | 750 | 0 | 2500 | 37 |

*Empty cell means data are not available

TABLE 3*

| Comparative Experiment | Catalyst type | I2.16 g/10 m | I21.6 g/10 m | I10/I2 — | Density g/cc | Mn g/mole | Mw g/mole | Mw/Mn — |
|---|---|---|---|---|---|---|---|---|
| A** | Ziegler | 0.011421 | 0.38 | | 0.9521 | 90300 | 468100 | 5.18 |
| B** | Ziegler | 0.009017 | 0.3 | | 0.9280 | 92800 | 461000 | 4.97 |
| C | Ziegler | 100.4 | | | 0.9730 | 4404 | 41095 | 9.33 |
| D | Ziegler | 0.56 | | | 0.9641 | | | |
| E | Ziegler | 0.94 | 56.9 | 12.3 | 0.9668 | 21350 | 135000 | 6.32 |
| F | Ziegler | 0.23 | 12.7 | 12.6 | 0.9615 | 33100 | 187800 | 5.67 |
| G | CGC | 1.51 | | 10.4 | 0.9586 | | | |
| H | CGC | 3.03 | | 9.1 | 0.9584 | | | |
| I | CGC | 0.25 | | 24.3 | 0.9550 | | | |
| J | CGC | 4.91 | | 8.6 | 0.9596 | | | |
| K | CGC | 23.2 | | 6.7 | 0.9645 | | | |
| L | CGC | 38.7 | | 7.1 | 0.9617 | | | |
| M | CGC | 15.2 | | 7.8 | 0.9618 | | | |
| N | CGC | 2.90 | | 8.6 | 0.9582 | | | |
| O | CGC | 0.67 | | 16.9 | 0.9552 | | | |
| P | CGC | 1.54 | | 13.2 | 0.9558 | | | |
| Q | CGC | 1.66 | | 13.0 | 0.9556 | | | |
| R | CGC | 2.50 | | 12.2 | 0.9567 | | | |
| S | CGC | 3.55 | | 10.3 | 0.9584 | | | |
| T | CGC | 1.40 | | 13.6 | 0.9558 | | | |
| U | CGC | 0.95 | | 15.4 | 0.9543 | | | |
| V | CGC | 3 | | 10.1 | 0.9580 | | | |
| W | CGC | 2.5 | | 10.5 | 0.9580 | | | |
| X | CGC | 1.6 | | 8.4 | 0.9560 | 45300 | 83400 | 1.84 |
| Y | CGC | 1.9 | | 10.5 | 0.9580 | 33300 | 66800 | 2.01 |
| Z | CGC | 4.2 | | 9.1 | 0.9580 | 30900 | 60700 | 1.96 |
| AA | CGC | 1.72 | | 12.1 | 0.9580 | 33700 | 66300 | 1.97 |
| AB | CGC | 1.00 | | 12 | 0.9580 | 34300 | 69100 | 2.01 |
| AC | bisCp/Borate | 0.30 | | 6.0 | 0.9478 | | | |
| AD | bisCp/Borate | 1.16 | | | 0.9545 | 35014 | 87466 | 2.50 |
| AE | bisCp/Borate | 2.29 | | | 0.9557 | 34130 | 95069 | 2.79 |
| AF | bisCp/Borate | 1.53 | | | 0.9557 | 34100 | 78700 | 2.31 |
| AG | bisCp/Borate | 1.19 | | | 0.9557 | | | |
| AH | bisCp/Borate | 3.78 | | | 0.9542 | | | |
| AI | IND/Borate | 0.53 | | 17.4 | 0.9548 | | | |
| AJ | nBuCp$_2$ZrCl$_2$ | 1.80 | | | 0.9565 | | | |
| AK | nBuCp$_2$ZrCl$_2$ | 4.82 | | | 0.9615 | | | |
| AL*** | nBuCp$_2$ZrCl$_2$ | 5 | | | 0.9552 | | 76000 | 2.80 |

*Empty cell means data are not available
**I2 is calculated from I21 using:
I2.16/I2.16 = (21.6/2.16)^(1/n) where log n = −0.1574 + 0.04645.log(I21.6)
From: Shenoy, A. V., Chattopadhyay, S., Nadkarni, V. M., Rheologica Acta, 1983, 22, 90
***Stehling et al. U.S. Pat. No. 5,382,631

TABLE 4

| Compara-tive Experi-ment | Slurry Process | | | | | | Solution Process | | | | |
|---|---|---|---|---|---|---|---|---|---|---|---|
| | Reactor temperature °C. | Reactor pressure bar | Ethylene flow g/hr | Hydrogen flow g/hr | Butene flow g/hr | Isopentane flow g/hr | Reactor level % | Solvent feed kg/hr | Ethylene feed kg/hr | Hydrogen feed Sml/min | Reactor tem-perature °C. | Ethyl-ene conver-sion % |
| A | 80 | 12 | | | 0 | | | — | — | — | — | — |
| B | 80 | 12 | | | | | | — | — | — | — | — |
| C | 80 | 12 | | | 0 | | | — | — | — | — | — |
| D | 85 | 6.8 | 3750000 | 12500 | — | 10800000* | 50 | — | — | — | — | — |
| E | 85 | 6.8 | 3750000 | 15600 | — | 10800000* | 50 | — | — | — | — | — |
| F | 85 | 6.5 | 3600000 | 10300 | — | 10800000* | 50 | — | — | — | — | — |
| G | — | — | — | — | — | — | — | 26.0 | 3.5 | 45 | 139.5 | 89 |
| H | — | — | — | — | — | — | — | 27.0 | 4 | 51 | 140 | 92 |
| I | — | — | — | — | — | — | — | 27.0 | 3.5 | 22 | 139 | 90 |
| J | — | — | — | — | — | — | — | 27.0 | 4 | 22 | 148 | 90 |
| K | — | — | — | — | — | — | — | 27.0 | 4 | 0 | 145 | 90 |
| L | — | — | — | — | — | — | — | 24.0 | 3.5 | 70 | 138.5 | 90 |
| M | — | — | — | — | — | — | — | 24.0 | 3.5 | 50 | 141 | 93 |
| N | — | — | — | — | — | — | — | 24.0 | 3.5 | 50 | 141 | 93 |
| O | — | — | — | — | — | — | — | 24.0 | 3.5 | 33 | 141 | 95 |

TABLE 4-continued

| | Slurry Process | | | | | | | Solution Process | | | | |
|---|---|---|---|---|---|---|---|---|---|---|---|---|
| Comparative Experiment | Reactor temperature °C. | Reactor pressure bar | Ethylene flow g/hr | Hydrogen flow g/hr | Butene flow g/hr | Isopentane flow g/hr | Reactor level % | Solvent feed kg/hr | Ethylene feed kg/hr | Hydrogen feed Sml/min | Reactor temperature °C. | Ethylene conversion % |
| P | — | — | — | — | — | — | — | 24.0 | 3.5 | 28.4 | 140 | 94 |
| Q | — | — | — | — | — | — | — | 24.0 | 3.5 | 31.5 | 136 | 95 |
| R | — | — | — | — | — | — | — | 24.0 | 3.5 | 31.5 | 136 | 95.5 |
| S | — | — | — | — | — | — | — | 24.0 | 3.5 | 31.5 | 136 | 95 |
| T | — | — | — | — | — | — | — | 24.0 | 3.5 | 31.5 | 135.5 | 93 |
| U | — | — | — | — | — | — | — | 24.0 | 3.5 | 31.5 | 138 | 94.5 |
| V | — | — | — | — | — | — | — | 24.0 | 3.5 | 31.6 | 140 | 93.5 |
| W | — | — | — | — | — | — | — | 24.0 | 3.5 | 31.5 | 132 | 91 |
| X | — | — | — | — | — | — | — | 24.0 | 3.5 | 34 | 140 | 85 |
| Y | — | — | — | — | — | — | — | 24.0 | 3.5 | 41 | 145 | 87 |
| Z | — | — | — | — | — | — | — | 28.2 | 3.5 | 46 | 145 | 90 |
| AA | — | — | — | — | — | — | — | 22.0 | 3.5 | 43 | 151 | 91 |
| AB | — | — | — | — | — | — | — | — | 3.5 | | 150 | 90 |
| AC | 75 | 12 | 750 | 0.3 | 0 | 4000 | 67 | — | — | — | — | — |
| AD | 65 | 15 | 1100 | 0.3 | 0 | 2500 | 65 | — | — | — | — | — |
| AE | 65 | 15 | 650 | 0.3 | 0 | 2500 | 65 | — | — | — | — | — |
| AF | 65 | 15 | 800 | 0.29 | 0 | 2500 | 65 | — | — | — | — | — |
| AG | 65 | 12 | 835 | 0.32 | 0 | 2000 | 65 | — | — | — | — | — |
| AH | 65 | 12 | 750 | 0.7 | 0 | 2000 | 45 | — | — | — | — | — |
| AI | 65 | 12 | 720 | 0.75 | 0 | 2000 | 40 | — | — | — | — | — |
| AJ | 65 | 12 | 650 | 0.375 | 0 | 2000 | 44 | — | — | — | — | — |
| AK | 65 | 12 | 700 | 0.55 | 0 | 2000 | 44 | — | — | — | — | — |
| AL | — | — | — | — | — | — | — | — | — | — | — | — |

*Empty cell means data are not available b) The Ethylene Homopolymers as Sintering Powders Examples 15 and 16 illustrate the improved modulus of elasticity, ball indentation hardness and notched impact strength of the ethylene homopolymers of the current invention as compared to commercial products used as sintering powders of similar molecular weight.

Example 15

The higher density ethylene homopolymer of Example 13 was used to prepare a sample for the notched impact strength, ball indentation hardness and modulus of elasticity tests the results of which are shown in Table 5.

Example 16

The sample was prepared as for Example 15 but used the ethylene homopolymer of Example 14

Comparative Experiments AM-AR

The samples were prepared as for Example 15 but the following commercial resins were used: AM=Lupolen HM071 (BASF), and AN=Hostalen GUR 8110, AO=Hostalen GUR 4113, AP=Hostalen GUR 4120, AQ=Hostalen GUR 4130, AR=Hostalen GUR 4150, all from Hoechst (see Table 5).

TABLE 5

| Property | Example 15 | Example 16 | Comp. Exp AM | Comp. Exp AN | Comp. Exp AO | Comp. Exp AP | Comp. Exp. AQ | Comp. Exp. AR |
|---|---|---|---|---|---|---|---|---|
| density g/cm$^3$ | 0.947 | | 0.950 | 0.950 | | | | |
| viscosity number (decaline) cm$^3$/g | 457 | 2048 | 460 | 510 | 1800 | 2300 | 2800 | 3500 |
| modulus of elasticity N/mm$^2$ | 1110 | 788 | 1000 | 1060 | 750 | 720 | 680 | 680 |
| ball indentation hardness N/mm$^2$ | 49 | 40 | 46 | 46 | 38 | 38 | 37 | 36 |
| Double notched impact strength kJ/m$^2$ | 210 | | 60 | $\leq 25$ | | | | | c) Blend Compositions Comprising The Ethylene Homopolymers

The individual components of the blend compositions of Examples 17 to 24 were prepared by the catalyst and polymerization process used for Example 1, the process conditions i.e. hydrogen and comonomer concentrations were adjusted to produce the components having the desired properties summarized in Table 6.

Example 17

Example 17 is a blend of 48% by weight of the ethylene homopolymer of the present invention having an $I_2$ of 26.4 g/10 min and a density of 0.9734 g/cm$^3$ and 52% by weight of a different ethylene homopolymer of the present invention having an $I_2$ of 0.01085 g/10 min and a density of 0.9484 g/cm$^3$. The blend was prepared in a Winkworth 2Z-blade mixer. This internal mixer is equipped with two mixing blades running at different rpm: the front screw rotates at 52 rpm, the rear screw at 30 rpm. The working capacity is 1.2 liters.

The powders were first dry blended with 2000 ppm Irganox® B225 available from Ciba Geigy. Charges of 350 g of the mixture of the desired composition were then loaded and mixed for 10 minutes at 190° C. After mixing the polymer is removed and is milled in a Heinrich Dreher S20 grinder. The ground polymer is then ready for compression molding.

Examples 18

Examples 18 is a blend of 48% by weight of the ethylene homopolymer of the present invention having an $I_2$ of 26.4 g/10 min and a density of 0.9734 g/cm$^3$ and and 52% by weight of an ethylene/butene-1 copolymer prepared under slurry process conditions and having a molecular weight maximum occurring in the fraction having the highest comonomer content and having an $I_2$ of 0.00194 g/10 min a density of 0.9203 g/cm$^3$. The blend was prepared as for Example 17

Examples 19-20

These blends were prepared as for Example 18 using the components and wt ratio's summarized in Table 6.

Examples 17-20 (Table 7) illustrate the surprising and dramatic improvement in room and low temperature impact properties of the various blends as measured by GC versus the commercial resins of Comparative Experiments AS-AV. They also demonstrate that excellent stress crack resistance is observed (as measured by PENT) while maintaining excellent processability (as measured by the viscosity numbers). These examples also show the surprising improvement in impact properties as the comonomer content of Component B is increased (as shown by its density). Examples 21-22 and Example 19 (Table 8) illustrate the surprising and dramatic improvement in room and low temperature impact properties of the various blends as measured by GC and in stress crack resistance (as measured by PENT) on increasing the molecular weight of Component B while maintaining modulus.

Example 21

Examples 21 is a blend of 48% by weight of the ethylene homopolymer of the present invention having an $I_2$ of 26.4 g/10 min and a density of 0.9734 g/cm$^3$ and and 52% by weight of an ethylene/butene-1 copolymer prepared under slurry process conditions and having a molecular weight maximum occurring in the fraction having the highest comonomer content and having an $I_2$ of 0.00083 g/10 min a density of 0.9128 g/cm$^3$. The blend was prepared as for Example 17.

Example 22

This blend was prepared as for Example 17 using the components and wt ratio's summarized in Table 6.

Example 23

Example 23 is a blend of 65% by weight of the ethylene homopolymer of the present invention having an $I_2$ of 8.65 g/10 min and a density of 0.9779 g/cm$^3$ and and 35% by weight of an ethylene/butene-1 copolymer prepared under slurry process conditions and having a molecular weight maximum occurring in the fraction having the highest comonomer content and having an $I_2$ of 0.00083 g/10 min a density of 0.9128 g/cm$^3$. The blend was prepared as for Example 17.

Example 24

This blend was prepared as for Example 17 using the components and wt ratio's summarized in Table 6.

Examples 17 to 24 illustrate that the excellent properties of the various blends as well and that their range in processability as measured by the viscosity at 100/s over a wide range of molecular weights and densities of Components A and B is similar to those of Comparative Materials AS to AV. Therefore it can be expected that materials can be fabricated that have at least equivalent extrudability on the machine as the comparative examples.

Comparative Experiments AS-AV are resins prepared using Ziegler and single site catalysts the properties of which are summarized in Table 10.

Comparative Experiment AS

Comparative Experiment AS is a ethylene/octene copolymer prepared under similar continuous solution process conditions as Comparative Experiment G using a Ziegler catalyst and is commercially available from the Dow Chemical Company under the tradename Dowlex™ 2344E and having the properties summarized in Table 10.

Comparative Experiment AT

Comparative Experiment AT is a ethylene/octene copolymer produced under similar continuous solution process conditions as Comparative Experiment G using a constrained geometry catalyst and having the properties summarized in Table 10.

Comparative Experiment AU

Comparative Experiment AU is a ethylene/octene copolymer prepared under similar continuous solution process conditions as Comparative Experiment G using a Ziegler catalyst and is commercially available from the Dow Chemical Company under the tradename Dowlex™ 5056.01 and having the properties summarized in Table 10.

Comparative Experiment AV

Comparative Experiment AV is a ethylene/octene copolymer prepared under similar continuous solution process conditions as Comparative Experiment G using a constrained geometry catalyst and having the properties summarized in Table 10.

Examples 25-26

The individual components of the blend compositions of Examples 25 and 26 were prepared using the following catalyst and polymerization procedure.

A sample of 6.2 g (8.8 mmol) of triethylammonium tris(pentafluorophenyl)(4-hydroxyphenyl)borate was dissolved in 4 liter of toluene which had been heated to and maintained at 90° C. for 30 minutes. To this solvent was added a 40 ml aliquot of a 1M solution of triehexylaluminum in toluene. The resultant mixture was stirred for 1 min at 90° C. On the other hand 100 g of silica P-10 (manufactured and sold by Fuji silysia, Japan), which had been treated at 500° C. for 3 hours in flowing nitrogen, was slurried in 1.7 liter of toluene. This silica slurry was heated to 90° C. To this silica slurry was added said mixture of triethylammonium tris(pentafluorophenyl)(4-hydroxy phenyl) borate and triethylaluminum keeping 90° C., and stirred for 3 hours at 90° C. To the resultant was added a 206 ml aliquot of a 1 M solution of trihexylaluminum in toluene. The resultant mixture in about 5.9 liter of toluene was stirred at 90° C. for 1 hours. Then the supernatant of the resultant mixture was removed by decantation method using 90° C. toluene to remove excess trihexylaluminum. The decantation was repeated 5 times. After that, a 20 ml aliquot of a dark violet colored 0.218M solution of titanium (N-1,1-dimethylethyl)dimethyl[1-(1,2,3,4,5,-eta)-2,3,4,5-tetramethyl-2,4-cyclopentadien-1-yl]silanaminato [(2-)N]-($\eta^4$-1,3-pentadiene) in ISOPAR™ E (manufactured and sold by Exxon Chemical Co., USA) was added to the mixture and the resultant mixture was stirred for 3 hours to thereby obtain a green colored solid catalyst system.

Hexane, ethylene, 1-butene, hydrogen and the solid catalyst system were continuously fed to a continuously stirred tank reactor. The flow rates of hexane, ethylene, and hydrogen and 1-butene were adjusted to give the desired properties molecular weight and density for each component of the blend. The butene flow rate used to prepare the copolymer Component B of Examples 25 and 26 was 0.11 kg/hr. The slurry product formed was continuously withdrawn from the reactor. The total pressure of the reactor was 10 atm and the internal temperature of the reactor was maintained at 80° C. The slurry withdrawn was fed to a flash tank to remove the diluent and the dry, free flowing ethylene copolymer powder was obtained.

The blends were prepared with using the twin-screw extruder (PCM-45, manufactured by IKEGAI, Co., Ltd., Japan). The screw rotates at 100-200 rpm. The mixing temperature was set up at 220° C. (screw barrel temperature).

The powders were first dry blended with 2000 ppm Irganox® 1076 available from Ciba Geigy, 600 ppm Calcium Stearate, and 1000 ppm P-EPQ® available from Sandoz.

The butene flow rate used to prepare the copolymer Component B of Examples 27 and 28 was 0.05 kg/hr Example 25

Examples 25 is a blend of 50% by weight of the ethylene homopolymer of the present invention having an $I_2$ of 67.3 g/10 min and a density of 0.9734 g/cm³ and and 50% by weight of an ethylene/butene-1 copolymer prepared under slurry process conditions and having a molecular weight maximum occurring in the fraction having the highest comonomer content and having an $I_2$ of 0.012 g/10 min a density of 0.9295 g/cm³.

Example 26

Examples 26 is a blend of 50% by weight of the ethylene homopolymer of the present invention having an $I_2$ of 380 g/10 min and a density of 0.9788 g/cm³ and and 50% by weight of an ethylene/butene-1 copolymer prepared under slurry process conditions and having a molecular weight maximum occurring in the fraction having the highest comonomer content and having an $I_2$ of 0.012 g/10 min a density of 0.9295 g/cm³.

Examples 27-28

The individual components of the blend compositions of Examples 27 and 28 were prepared using the same polymerization and blending process used for Examples 25 and 26, however the butene flow rate used to prepare the copolymer Component B of Examples 27 and 28 was 0.05 kg/hr and the following catalyst preparation was used.

200 g of silica P-10 (manufactured and sold by Fuji silysia, Japan), which had been treated at 500° C. for 3 hours in flowing nitrogen, was slurried in 5 liter of hexane. To the resultant slurry was added a 400 ml aliquot of a 1 M solution of triethylaluminum in hexane. The resultant mixture was stirred for 0.5 hour at room temperature. To this slurry was added a solution of 20.1 g (17.6 mmol) of bis(hydrogenated tallowalkyl)methylammonium tris(pentafluorophenyl)(4-hydroxyphenyl)borate in 296 ml of toluene. The resultant mixture was stirred for 0.5 hour at room temperature. After that, a 60 ml aliquot of a dark violet colored 0.218M solution of titanium (N-1,1-dimethylethyl)dimethyl[1-(1,2,3,4,5,-eta)-2,3,4,5-tetramethyl-2,4-cyclopentadien-1-yl]silanaminato[(2-)N]-($\eta^4$-1,3-pentadiene) in ISOPAR™ E (manufactured and sold by Exxon Chemical Co., USA) was added to the mixture and the resultant mixture was stirred for 3 hours at room temperature to thereby obtain a green colored solid catalyst system.

Example 27

Examples 27 is a blend of 50% by weight of the ethylene homopolymer of the present invention having an $I_2$ of 380 g/l 10 min and a density of 0.9788 g/cm³ and and 50% by weight of an ethylene/butene-1 copolymer prepared under slurry process conditions and having a molecular weight maximum occurring in the fraction having the highest comonomer content and having an $I_2$ of 0.013 g/10 min a density of 0.9378 g/cm³.

Example 28

Example 28 is a blend of 50% by weight of the ethylene homopolymer of the present invention having an $I_2$ of 380 g/10 min and a density of 0.9788 g/cm³ and and 50% by weight of an ethylene/butene-1 copolymer prepared under slurry process conditions and having a molecular weight maximum occurring in the fraction having the highest comonomer content and having an $I_2$ of 0.013 g/10 min a density of 0.9378 g/cm³.

Comparative Example AW-AY

The ethylene homopolymer used as Component A was produced using a Ziegler-Natta catalyst under slurry process conditions. The ethylene copolymers used as Component B were produced using a Ziegler-Natta catalyst substantially similar to those particularly useful for the preparation of heterogeneous polymers under slurry process conditions as described herein. The Ziegler-Natta catalyst had about 2 wt % of Ti on the surface of the support comprising mainly magnesium dichloride.

Comparative Example AW

Example AW is a blend of 50% by weight of the ethylene homopolymer produced using a Ziegler catalyst having an $I_2$ of 113 g/10 min and a density of 0.9753 g/cm$^3$, and 50% by weight of an ethylene/butene-1 copolymer prepared under slurry process conditions using a Ziegler catalyst and having an $I_2$ of 0.015 g/10 min and a density of 0.9306 g/cm$^3$.

Comparative Example AX

Example AX is a blend of 50% by weight of the ethylene homopolymer produced using a Ziegler catalyst having an $I_2$ of 280 g/10 min and a density of 0.9795 g/cm$^3$ and 50% by weight of an ethylene/butene-1 copolymer prepared under slurry process conditions using a Ziegler catalyst and having an $I_2$ of 0.015 g/10 min and a density of 0.9306 g/cm$^3$.

Comparative Example AY

Comparative Example AY is a blend of 60% by weight of the ethylene homopolymer produced using a Ziegler catalyst having an $I_2$ of 280 g/10 min and a density of 0.9795 g/cm$^3$ and 40% by weight of an ethylene/butene-1 copolymer prepared under slurry process conditions using a Ziegler catalyst and having an $I_2$ of 0.015 g/10 min and a density of 0.9306 g/cm$^3$.

The polymer properties for Component A and Component B of these blend formulation are summarized in Table 11. The results of the testing of the various blend compositions are shown in Table 12.

Examples 25-28 show the excellent balance of properties such as impact strength at low temperature (as measured by Charpy Impact Strength −20° C.), processability (as measured by $I_{21.6}$), and ESCR (as measured by Bending ESCR TEST) for the various blend compositions and such balance is best achieved by having the comonomer preferentially in the high molecular weight component. Further, it is clear that the Example 25-28 exhibit the superior properties comparing to the Comparative Examples AW-AY

TABLE 6

| Example # | Low $M_w$ Ethylene Homopolymer (Component A) | | | High $M_w$ Ethylene Interpolymer (Component B) | | | |
|---|---|---|---|---|---|---|---|
| | $I_2$ g/10 min | wt % in blend | density g/cm$^3$ | $I_2$ g/10 min | wt % in blend | mole % butene | density g/cm$^3$ |
| 17 | 26.4 | 48 | 0.9734 | 0.01085 | 52 | 0 | 0.9484 |
| 18 | 26.4 | 48 | 0.9734 | 0.00194 | 52 | 1.45 | 0.9203 |
| 19 | 26.4 | 48 | 0.9734 | 0.01085 | 52 | 2.91 | 0.9148 |
| 20 | 26.4 | 48 | 0.9734 | 0.00872 | 52 | 5.96 | 0.9033 |
| 21 | 26.4 | 0 | 0.9734 | 0.00083 | | 3.12 | 0.9128 |
| 22 | 26.4 | 0 | 0.9734 | 0.13 | | 3.1 | 0.9175 |
| 23 | 8.65 | 0 | 0.9779 | 0.00083 | | 3.12 | 0.9128 |
| 24 | 8.65 | 0 | 0.9779 | 0.13 | | 3.1 | 0.9175 |

TABLE 7

| | Units | Example # | | | |
|---|---|---|---|---|---|
| | | 17 | 18 | 19 | 20 |
| Melt Flow Properties | | | | | |
| $I_2$ | g/10 min | 0.1 | — | 0.09 | 0.08 |
| $I_5$ | g/10 min | 0.32 | 0.08 | 0.31 | 0.28 |
| $I_{10}$ | g/10 min | 1.05 | 0.27 | 1 | 0.86 |
| $I_{21.6}$ | g/10 min | 4.91 | 1.82 | 4.99 | 5.02 |
| $I_{10}/I_2$ | | 10.5 | — | 11.1 | 10.8 |
| $I_{21.6}/I_5$ | | 15.3 | 22.8 | 16.1 | 17.9 |
| $I_{21.6}/I_2$ | | 49.1 | — | 55.4 | 62.8 |
| Density | g/cm$^3$ | 0.962 | 0.946 | 0.942 | 0.9349 |
| IR Butene Content | Mole % | 0 | 0.85 | 1.64 | 3.13 |
| Density Calc. | g/cm$^3$ | 0.9628 | 0.9422 | 0.9371 | 0.931 |
| GPC Analysis | | | | | |
| $M_n$ | g/mole | 27100 | 29200 | 28400 | 29500 |
| $M_w$ | g/mole | 229000 | 310000 | 201000 | 212000 |
| $M_n/M_w$ | — | 8.45 | 10.62 | 7.08 | 7.19 |
| Rheology Bohlin | | | | | |
| Viscosity at 0.1 l/s | Pa · s | 60898 | 189326 | 49320 | 60305 |
| Viscosity at 100 l/s | Pa · s | 2905 | 3807 | 2572 | 2564 |
| Mechanical Properties | | | | | |
| Tensile Properties | | | | | |
| Yield Stress | Mpa | 29.48 | 21.23 | 18.65 | 14.96 |
| Ultim. Stress | Mpa | 36.31 | 27.42 | 29.48 | 31.89 |
| Elongation | % | 750 | 484 | 555 | 558 |
| Toughness | Mpa | 174 | 91 | 103 | 102 |
| Slope SH | Mpa | 5.36 | 4.63 | 4.48 | 5.02 |
| 2% Sec. Mod. | Mpa | 867 | 572 | 534 | 417 |
| Young's Modulus | Mpa | 1104 | 710 | 674 | 503 |

TABLE 7-continued

|  | Units | Example # 17 | Example # 18 | Example # 19 | Example # 20 |
|---|---|---|---|---|---|
| Impact Properties |  |  |  |  |  |
| Gc +20 C. | kJ/m$^2$ | 54.1 | 38.4 | 34.6 | 71.5 |
| Gc +0 C. | kJ/m$^2$ | 41.4 | 30.5 | 29.2 | 61.3 |
| Gc −20 C. | kJ/m$^2$ | 41.4 | 23.9 | 20.2 | 40.8 |
| PENT |  |  |  |  |  |
| 2.4 Mpa | Min. | 120 | >100000 | >100000 | >100000 |
| Intrinsic Tear | g/mil. | 69 | 151 | 206 | 282 |
| Haze | % [0.5 mm] | 100 | 84.5 | 94.6 | 98.4 |

TABLE 8

|  | Units | Example # 19 | Example # 21 | Example # 22 |
|---|---|---|---|---|
| Melt Flow Properties |  |  |  |  |
| $I_2$ | g/10 min | 0.09 | — | 0.57 |
| $I_5$ | g/10 min | 0.31 | 0.08 | 1.86 |
| $I_{10}$ | g/10 min | 1 | 0.32 | 5.3 |
| $I_{21.6}$ | g/10 min | 4.99 | 2.42 | 21 |
| $I_{10}/I_2$ |  | 11.1 | — | 9.3 |
| $I_{21.6}/I_5$ |  | 16.1 | 30.3 | 11.3 |
| $I_{21.6}/I_2$ |  | 55.4 | — | 36.8 |
| Density | g/cm$^3$ | 0.942 | 0.9448 | 0.9427 |
| IR Butene | Mole % | 1.64 | 1.39 | 1.75 |
| Density Calc. | g/cm$^3$ | 0.9371 | 0.9372 | 0.9397 |
| GPC Analysis |  |  |  |  |
| $M_n$ | g/mole | 28400 | 22000 | 24600 |
| $M_w$ | g/mole | 201000 | 335000 | 133000 |
| $M_n/M_w$ | — | 7.08 | 15.23 | 5.41 |
| Rheology Bohlin |  |  |  |  |
| Viscosity at 0.1 l/s | Pa·s | 49320 | 247070 | 12131 |
| Viscosity at 100 l/s | Pa·s | 2572 | 3389 | 1638 |
| Mechanical Properties Tensile Properties |  |  |  |  |
| Yield Stress | Mpa | 18.65 | 20.17 | 18.59 |
| Ultim. Stress | Mpa | 29.48 | 33.99 | 30.11 |
| Elongation | % | 555 | 566 | 672 |
| Toughness | Mpa | 103 | 115 | 126 |
| Slope SH | Mpa | 4.48 | 5.59 | 3.91 |
| 2% Sec. Mod. | Mpa | 534 | 557 | 541 |
| Young's Modulus | Mpa | 674 | 696 | 672 |
| Impact Properties |  |  |  |  |
| Gc +20 C. | kJ/m$^2$ | 34.6 | 40.2 | 25.2 |
| Gc +0 C. | kJ/m$^2$ | 29.2 |  |  |
| Gc −20 C. | kJ/m$^2$ | 20.2 | 20.3 | 6 |
| PENT |  |  |  |  |
| 2.4 Mpa | Min. | >100000 | >100000 | 59100 |
| Intrinsic Tear | g/mil. | 206 | 190 | 148 |
| Haze | % [0.5 mm] | 94.6 | 94 | 98.8 |

TABLE 9

|  | Units | Example # 19 | Example # 23 | Example # 24 |
|---|---|---|---|---|
| Melt Flow Properties |  |  |  |  |
| $I_2$ | g/10 min | 0.09 | 0.05 | 0.25 |
| $I_5$ | g/10 min | 0.31 | 0.21 | 0.79 |
| $I_{10}$ | g/10 min | 1 | 1 | 2.25 |
| $I_{21.6}$ | g/10 min | 4.99 | 6.54 | 8.02 |
| $I_{10}/I_2$ |  | 11.1 | 20 | 9 |
| $I_{21.6}/I_5$ |  | 16.1 | 31.1 | 10.2 |
| $I_{21.6}/I_2$ |  | 55.4 | 130.8 | 32.1 |
| Density | g/cm$^3$ | 0.942 | 0.9497 | 0.9346 |
| IR Butene | Mole % | 1.64 | 1.28 | 2.32 |
| Density Calc. | g/cm$^3$ | 0.9371 | 0.9401 | 0.9294 |
| GPC Analysis |  |  |  |  |
| $M_n$ | g/mole | 28400 | 30900 | 38300 |
| $M_w$ | g/mole | 201000 | 288000 | 160000 |
| $M_n/M_w$ | — | 7.08 | 9.32 | 4.18 |
| Rheology Bohlin |  |  |  |  |
| Viscosity at 0.1 l/s | Pa·s | 49320 | 111427 | 22627 |
| Viscosity at 100 l/s | Pa·s | 2572 | 2316 | 2496 |
| Mechanical Properties Tensile Properties |  |  |  |  |
| Yield Stress | Mpa | 18.65 | 20.96 | 15.47 |
| Ultim. Stress | Mpa | 29.48 | 27.19 | 33.4 |
| Elongation | % | 555 | 553 | 691 |
| Toughness | Mpa | 103 | 101 | 132 |
| Slope SH | Mpa | 4.48 | 4.24 | 4.24 |
| 2% Sec. Mod. | Mpa | 534 | 617 | 420 |
| Young's Modulus | Mpa | 674 | 782 | 520 |
| Impact Properties |  |  |  |  |
| Gc +20 C. | kJ/m$^2$ | 34.6 | 38.4 | 41.3 |
| Gc +0 C. | kJ/m$^2$ | 29.2 | 25.6 | 29.8 |
| Gc −20 C. | kJ/m$^2$ | 20.2 | 18.1 | 13.2 |
| PENT |  |  |  |  |
| 2.4 Mpa | Min. |  |  |  |
| Intrinsic Tear | g/mil. |  |  |  |
| Haze | % [0.5 mm] |  |  |  |

TABLE 10

|  | Units | AS | AT | AU | AV |
|---|---|---|---|---|---|
| Melt Flow Properties | | | | | |
| $I_5$ | g/10 min | 0.77 | 0.41 | 1.12 | 0.43 |
| $I_{10}$ | g/10 min | 5.79 | 5.07 | 8.44 | 6.09 |
| $I_{21.6}$ | g/10 min | 21.02 | 19.5 | 30.29 | 23.77 |
| $I_{10}/I_2$ | — | | 7.52 | 12.37 | 7.54 | 14.16 |
| $I_{21.6}/I_5$ | — | | | | |
| $I_{21.6}/I_2$ | — | | 27.3 | 47.5 | 27 | 62.6 |
| Density (meas) | g/cm³ | 0.9356 | 0.9284 | 0.9203 | 0.9188 |
| Ir Analysis | | | | | |
| Octene Content | mole % | 0.79 | 0.85 | 2.86 | 1.86 |
| Gpc Analysis | | | | | |
| Mw | g/mole | 127000 | 95500 | 106000 | 95200 |
| $M_w/M_n$ | — | 3.41 | 2.11 | 3.30 | 2.07 |
| Rheology Bohlin | | | | | |
| Viscosity at 0.1 l/S | Pa·s | *10715* | *25817* | *7357* | *86443* |
| Viscosity. At 100 l/S | Pa·s | *1986* | *1643* | *1604* | *4480* |
| Tensiles | | | | | |
| Yield Stress | MPa | 16.29 | 13.52 | 9.34 | 10.08 |
| Ultimate Stress | MPa | 39.76 | 35.73 | 35.24 | 35.56 |
| Elongation | % | 926 | 823 | 975 | 856 |
| 2% Sec Modulus | MPa | 278 | 213 | 113 | 113 |
| Young Modulus | MPa | 508 | 378 | 166 | 196 |
| Toughness | MPa | 195 | 161 | 176 | 158 |
| Slope SH | MPa | 4.36 | 4.27 | 3.68 | 4.19 |
| Impact Properties | | | | | |
| Gc 0° C. | kJ/M² | 6.2 | 13.4 | 95.9 | 96 |
| Gc −20° C. | kJ/M² | 4.8 | 5 | 12.7 | 16.8 |
| Intrinsic Tear | g/mil | 144 | 264 | 551 | 432 |
| Haze | % [.5 mm] | 88.4 | 78.2 | 87.9 | |

*Note: italic values are calculated

TABLE 11

| | Low Mw Component (Component A) | | | | | High Mw Component (Component B) | | | | |
|---|---|---|---|---|---|---|---|---|---|---|
| Example # | $I_2$ g/10 min | mole % butene | Mw g/mol | Mw/Mn | density g/cm³ | wt % in blend | $I_2$ g/10 min | mole % butene | density g/cm³ | Mw g/mol | Mw/Mn | wt % in blend |
| Example 25 | 67.3 | 0 | 23000 | 3.20 | 0.9734 | 50 | 0.012 | 0.76 | 0.9295 | 297000 | 5.50 | 50 |
| Example 26 | 380 | 0 | 17200 | 3.30 | 0.9788 | 50 | 0.012 | 0.76 | 0.9295 | 297000 | 5.50 | 50 |
| Example 27 | 380 | 0 | 17200 | 3.30 | 0.9788 | 50 | 0.013 | 0.16 | 0.9378 | 487000 | 5.81 | 50 |
| Example 28 | 380 | 0 | 17200 | 3.30 | 0.9788 | 60 | 0.013 | 0.16 | 0.9378 | 487000 | 5.81 | 40 |
| Comp. Ex. AW | 113 | 0 | 79000 | 14.80 | 0.9753 | 50 | 0.015 | 0.95 | 0.9306 | 425000 | 7.64 | 50 |
| Comp. Ex. AX | 280 | 0 | 65000 | 16.20 | 0.9795 | 50 | 0.015 | 0.95 | 0.9306 | 425000 | 7.64 | 50 |
| Comp. Ex. AY | 280 | 0 | 65000 | 16.20 | 0.9795 | 60 | 0.015 | 0.95 | 0.9306 | 425000 | 7.64 | 40 |

TABLE 12

| | UNITS | EXAMPLE 25 | EXAMPLE 26 | EXAMPLE 27 | EXAMPLE 28 | COMPARATIVE EX. AW | COMPARATIVE EX. AX | COMPARATIVE EX. AY |
|---|---|---|---|---|---|---|---|---|
| MELT FLOW PROPERTIES | | | | | | | | |
| $I_2$ | G/10 MIN | 0.12 | 0.12 | 0.13 | 0.30 | 0.13 | 0.18 | 0.40 |
| $I_5$ | G/10 MIN | 0.51 | 0.49 | 0.45 | 1.29 | 0.54 | 0.74 | 1.84 |
| $I_{21.6}$ | G/10 MIN | 10.9 | 10.8 | 11.6 | 37.0 | 13.9 | 20.1 | 55.5 |
| $I_{21.6}/I_2$ | | 90.8 | 89.8 | 92.0 | 125.5 | 109.5 | 111.4 | 139.1 |
| DENSITY | G/CM3 | 0.9552 | 0.9560 | 0.9613 | 0.9649 | 0.9551 | 0.9560 | 0.9603 |

TABLE 12-continued

|  | UNITS | EXAMPLE 25 | EXAMPLE 26 | EXAMPLE 27 | EXAMPLE 28 | COMPARATIVE EX. AW | COMPARATIVE EX. AX | COMPARATIVE EX. AY |
|---|---|---|---|---|---|---|---|---|
| IMPACT PROPERTIES |  |  |  |  |  |  |  |  |
| CHARPY +23 C. | KGFCM/CM2 | 24.4 | 20.6 | 31.0 | 12.2 | 17.6 | 13.5 | 6.6 |
| CHARPY 20 C. | KGFCM/CM2 | 19.0 | 13.0 | 20.6 | 8.0 | 12.5 | 5.2 | 2.7 |
| ESCR |  |  |  |  |  |  |  |  |
| BEND- 80 C. | HR. | 800 | >2,000 | 25 | <10 | 170 | 400 | 20 |
| ING 50 C. | HR. | >2,000 | >2,000 | 330 | 140 | 1,000 | >2,000 | 360 |

What is claimed is:

1. A process for forming a polymer blend composition, which process comprises:
   (I) preparing an ethylene homopolymer by a process, which process comprises polymerizing ethylene under slurry process conditions with a catalyst comprising;
      i) a supported catalyst component resulting from admixing:
         (A) a support material;
         (B) an organometal compound comprising a metal selected from Groups 2-13 of the Periodic Table of the Elements, germanium, tin, or lead;
         (C) an activator compound containing a cation which is capable of reacting with a transition metal compound to form a catalytically active transition metal complex, and a compatible anion having up to 100 nonhydrogen atoms and containing at least one substituent comprising an active hydrogen moiety; and
         (D) a transition metal compound; or
      ii) a supported catalyst component resulting from admixing
         (A) a support material and an alumoxane which component contains 15 to 40 weight percent of aluminum, based on the total weight of the support material and alumoxane, which is obtained by;
            (a) heating said support material and alumoxane under an inert atmosphere for a period and at a temperature sufficient to fix alumoxane to the support material, to provide a supported catalyst component wherein not more than about 10 percent aluminum present in the supported catalyst component is extractable in a one-hour extraction with toluene at 90° C. using about 10 ml toluene per gram of supported catalyst component; and
            (b) optionally, subjecting the product produced in step (a) to one or more wash steps to remove alumoxane not fixed to the support material; and
         (B) a transition metal compound; or
      iii) any combination of (i) and (ii);
   (II) contacting under polymerization conditions a feedstream comprising ethylene, optionally at least one α-olefin comonomer, and an ethylene polymerization catalyst, to form (B) an ethylene homopolymer or ethylene/α-olefin interpolymer; and
   (III) combining the ethylene homopolymer (A) with the ethylene homopolymer or ethylene/α-olefin interpolymer (B) to form (C) the polymer blend composition.

2. The process of claim 1 wherein steps (I) and (II) are performed in different reactors.

3. The process of claim 2 wherein the reactors are operated in series and step (I) is performed in the first reactor(s) and step (II) is performed in the second reactor(s); or, optionally, step (II) is performed in the first reactor(s) and step (I) is performed in the second reactor(s).

4. The process of claim 1 wherein;
   (a) step (II) is performed under slurry phase polymerization conditions, or solution phase polymerization conditions, or gas phase polymerization conditions; and
   (b) the ethylene polymerization catalyst used in step (II) is a Ziegler catalyst, or an unsupported single site catalyst, or a supported single site catalyst, or a mixture of any two or more of said ethylene polymerization catalysts.

5. The process of claim 4 wherein;
   (c) said supported single site catalyst comprises a supported constrained geometry catalyst.

6. The process of claim 1 wherein the ethylene polymerization catalyst of step (II) is:
   (I) a supported catalyst component resulting from admixing:
      (A) a support material;
      (B) an organometal compound comprising a metal selected from Groups 2-13 of the Periodic Table of the Elements, germanium, tin, or lead;
      (C) an activator compound containing a cation which is capable of reacting with a transition metal compound to form a catalytically active transition metal complex, and a compatible anion having up to 100 nonhydrogen atoms and containing at least one substituent comprising an active hydrogen moiety; and
      (D) a transition metal compound; or
   (II) a supported catalyst component resulting from admixing
      (A) a support material and an alumoxane which component contains 15 to 40 weight percent of aluminum, based on the total weight of the support material and alumoxane, which is obtained by;
         (a) heating said support material and alumoxane under an inert atmosphere for a period and at a temperature sufficient to fix alumoxane to the support material, to provide a supported catalyst component wherein not more than about 10 percent aluminum present in the supported catalyst component is extractable in a one-hour extraction with toluene at 90° C. using about 10 ml toluene per gram of supported catalyst component; and
         (b) optionally, subjecting the product produced in step (a) to one or more wash steps to remove alumoxane not fixed to the support material; and
      (B) a transition metal compound; or
   (III) any combination of (I) and (II).

7. The process of claim 1 wherein the ethylene polymerization catalyst of step (II) is a Ziegler ethylene polymerization catalyst comprising;
   (a) a solid support component is a magnesium halide or silica, and (b) a transition metal component represented by the formulas:

$TrX'_{4-q}(OR^1)_q, TrX'_{4-q}R^2_q, VOX'_3$ and $VO(OR^1)_3$,
wherein:

Tr is a Group IVB, VB, or VIB metal, q is 0 or a number equal to or less than 4, X' is a halogen, and $R^1$ is an alkyl group, aryl group or cycloalkyl group having from 1 to 20 carbon atoms, and $R^2$ is an alkyl group, aryl group, aralkyl group, or substituted aralkyl group.

8. The process of claim 2 wherein the reactors are operated in parallel.

9. The process of claim 1 wherein the α-olefin interpolymer of step (II) has a lower density and a higher molecular weight than the homopolymer produced in step (I).

10. The process of claim 1 wherein the comonomer of step (II) is a $C_3$-$C_{20}$ α-olefin.

11. The process of claim 1 wherein the comonomer of step (II) is propylene, 1-butene, 1-pentene, 4-methyl-1-pentene, 1-hexene or 1-octene.

* * * * *